United States Patent
Gannedahl

(10) Patent No.: US 9,757,404 B2
(45) Date of Patent: Sep. 12, 2017

(54) COMBINATION COMPRISING AN OMEGA-3 FATTY ACID COMPOSITION AND AN SGLT2 INHIBITOR

(71) Applicant: AstraZeneca AB, Södertälje (SE)

(72) Inventor: Karl Erik Goeran Gannedahl, Mölndal (SE)

(73) Assignee: ASTRAZENECA AB, Södertälje (SE)

( * ) Notice: Subject to any disclaimer, the term of this patent is extended or adjusted under 35 U.S.C. 154(b) by 0 days.

(21) Appl. No.: 14/863,561

(22) Filed: Sep. 24, 2015

(65) Prior Publication Data

US 2016/0113953 A1 Apr. 28, 2016

Related U.S. Application Data

(60) Provisional application No. 62/055,055, filed on Sep. 25, 2014, provisional application No. 62/075,471, filed on Nov. 5, 2014.

(51) Int. Cl.
*A61K 31/202* (2006.01)
*A61K 31/7034* (2006.01)
*A61K 45/06* (2006.01)

(52) U.S. Cl.
CPC ........ *A61K 31/7034* (2013.01); *A61K 31/202* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,414,126 B1 | 7/2002 | Ellsworth et al. | |
| 6,515,117 B2 | 2/2003 | Ellsworth et al. | |
| 2008/0004336 A1 | 1/2008 | Gougoutas et al. | |
| 2008/0045466 A1 | 2/2008 | Katsuno et al. | |
| 2014/0107200 A1 | 4/2014 | Fawzy et al. | |
| 2014/0187633 A1 | 7/2014 | Manku et al. | |

FOREIGN PATENT DOCUMENTS

| | | |
|---|---|---|
| CN | 102755350 A | 10/2012 |
| EP | 2236137 A1 | 10/2010 |
| EP | 2428217 A1 | 3/2012 |
| WO | 2014142364 A2 | 9/2014 |

OTHER PUBLICATIONS

A Study to Investigate Effects of Omega-3 Carboxylic Acids and Dapagliflozin on Liver Fat Content in Diabetic Patients (EFFECTII), ClinicalTrials.gov Identifier: NCT02279407, Oct. 29, 2014.
Balasubramanian et al., Diabetic Medicine, 2010, vol. 27, pp. 150-156.
Bolinder et al., J Clin Endocrinol Metab, Mar. 2012; vol. 97(3), pp. 1020-31.
Cree et al, Mechanisms of Ageing and Development, 2007, vol. 128, pp. 558-565.
Chalasani et al, Gastroenterology, 2012, vol. 142, pp. 1592-1609.
Edvardsson et al, J Lipid Research, 2006, vol. 47, pp. 329-340.
Harris et al, Curr Opin Lipidol, 2006, vol. 17, pp. 387-393.
Kleiner et al, Hepatology, 2006, vol. 41(6), pp. 1313-1321.
Kwok et al, Aliment Pharmacol Ther, 2014, vol. 39, pp. 254-269.
Moore JB., Proc Nutr Soc, 2010, vol. 69, pp. 211-20.
Nobili et al, Plos One, 2014, vol. 9(2), p. e88005.
Oscarsson, J et al; "Association of Faecal Elastase-1 with Non-Fasting Triglycerides in Type 2 Diabetes", 2015.
Parker et al, J Hepatology, 2012, vol. 56, pp. 944-951.
Rathmann et al; Pancreatology, 2015, vol. 15, pp. 620-625.
Rathmann et al ; European Pancreatic Club 47th annual meeting, Jun. 24-26 2015: abstract, Association of fecal elastase 1 with no-fasting triglycerides in T2DM.
Rathmann et al, EASD Sep. 14-18, 2015; Association of fecal elastase 1 with no-fasting triglycerides in Type 2 Diabetes.
Rathmann et al, EASD Sep. 14-18, 2015; inverse association of fecal elastase 1in people without diabetes.
Rathmann, W et al; Inverse Association of HbA1c with Faecal Elastase 1 in People without Diabetes—2015.
Sanyal et al, Gastroenterology, 2014, vol. 147, pp. 377-384.
Sanyal et al, New England J Medicine, 2010, vol. 362(18), pp. 1675-1685.
Stevens et al, Digestive Diseases and Sciences, 2004, vol. 49:9, pp. 1405-1411.
Tomeno et al, Expert opin. Emerging Drugs, 2013, vol. 18(3), pp. 279-290.
Tahara et al, Eur J Pharmacology, 2013, vol. 715, pp. 246-255.
Rathmann W et al; Association of Faecal Elastase 1 with Non-Fasting Triglycerides in Type 2 diabetes—2015.
Washburn, J Med Chem, 2009, vol. 52(7), pp. 1785-1794.
Williams et all., Gastroenterology 2011, vol. 140, pp. 124-131.
Younossi et al, Aliment Pharmacol Ther, 2014, vol. 39, pp. 3-14.
Oscarsson et al, AASLD 2016, Abstract.

*Primary Examiner* — Layla Berry

(57) ABSTRACT

A method for treating NAFLD and/or NASH and suitable compositions for carrying out the method are claimed.

17 Claims, 4 Drawing Sheets

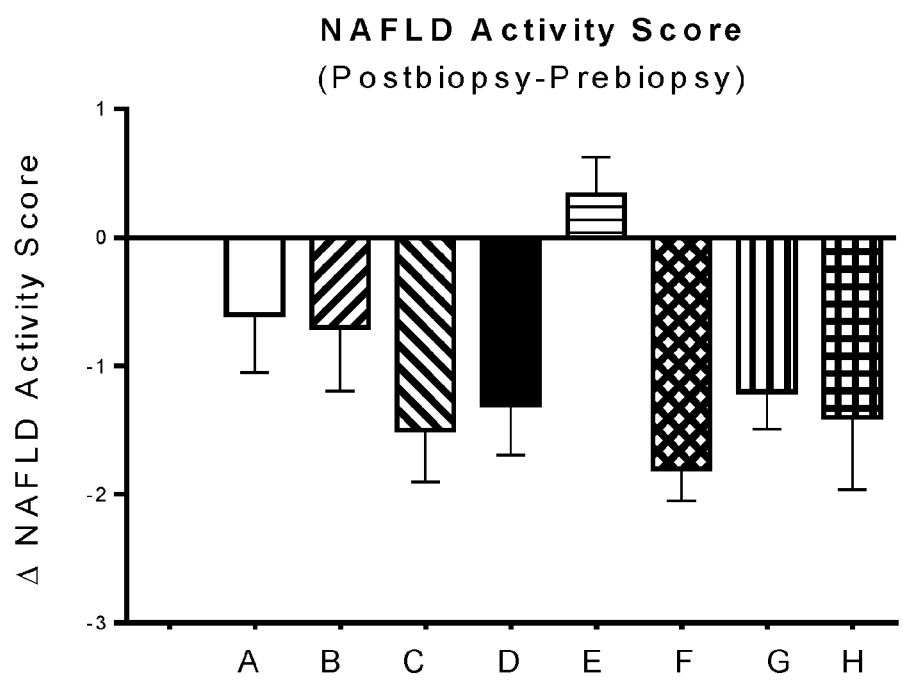
Figure 1: Effects of SGLT-2 inhibitors and Epanova alone and in combination on NAFLD activity score.

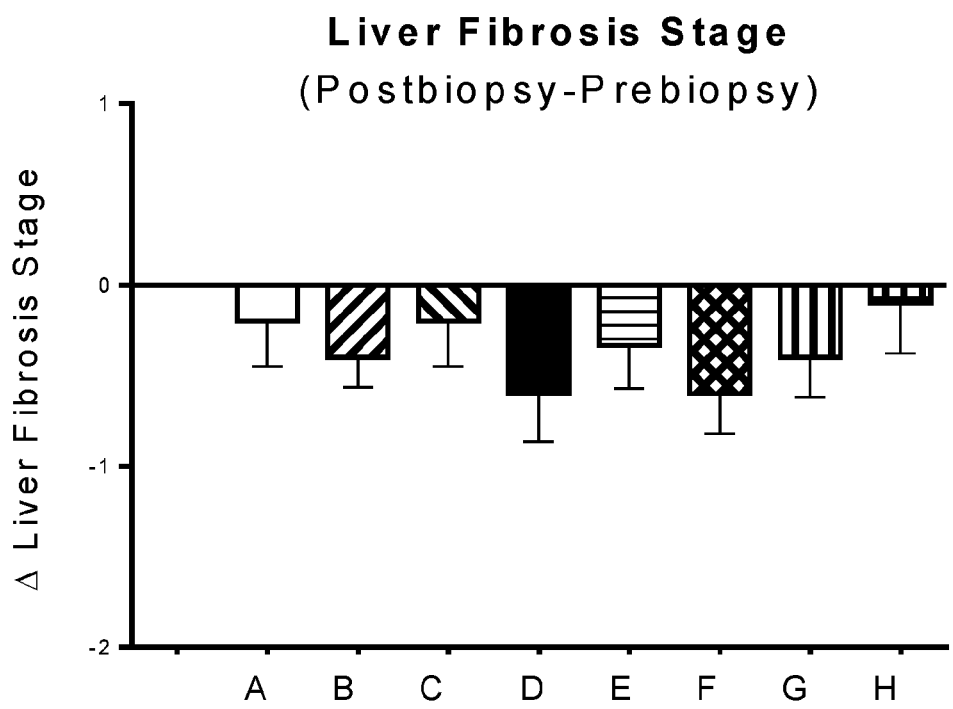
Figure 2: Effects of SGLT-2 inhibitors and Epanova alone and in combination on fibrosis stage.

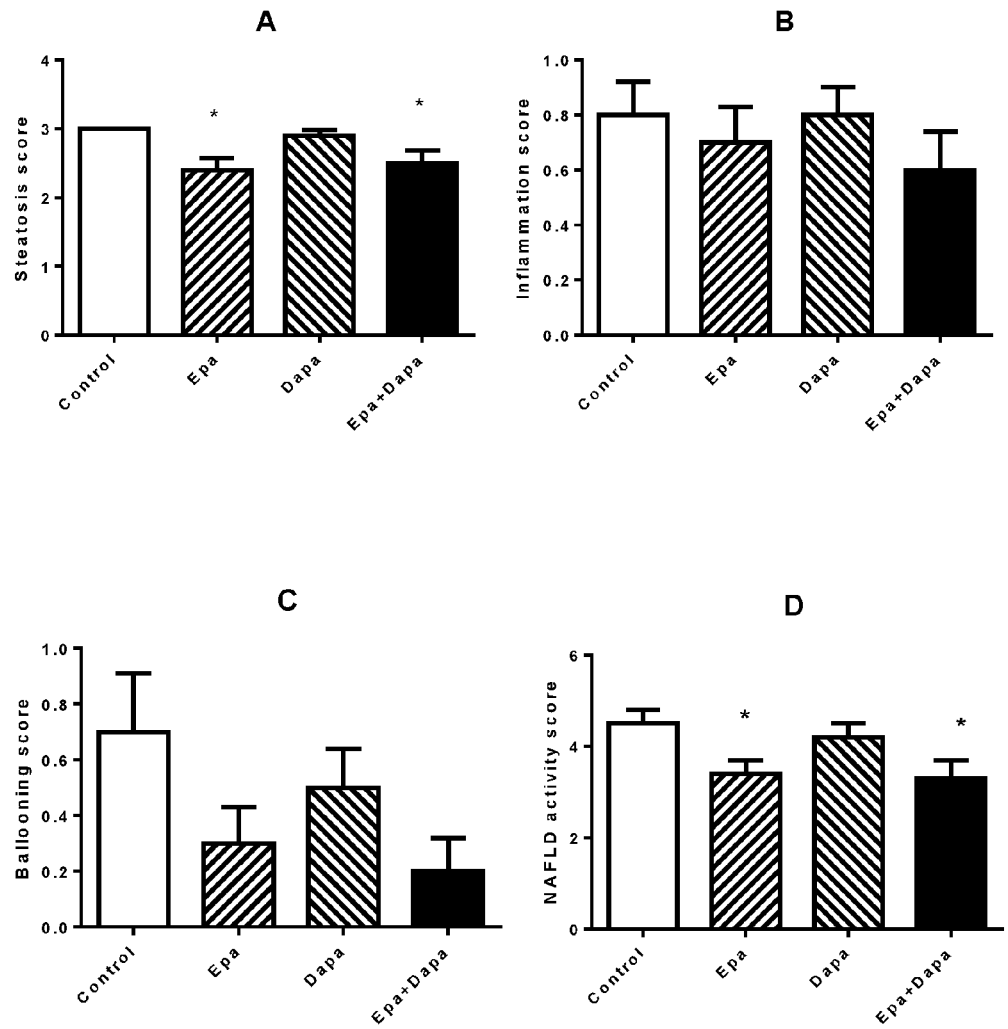
Figure 3: Effects of Epanova (Epa) and/or Dapagliflozin (Dapa)

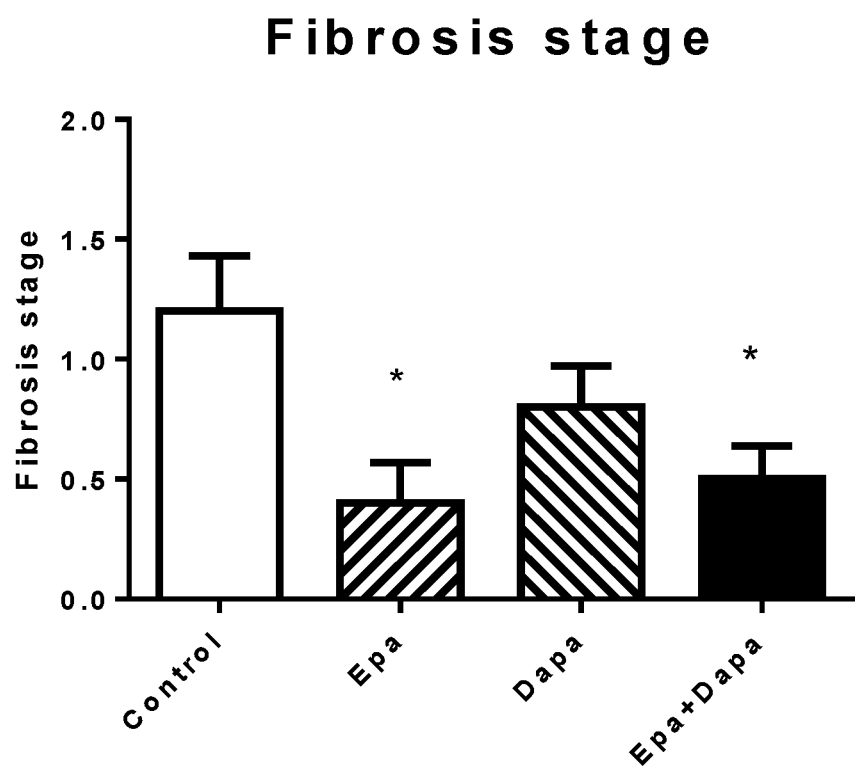
Figure 4: Effects of Epanova (Epa) and/or Dapagliflozin (Dapa)

COMBINATION COMPRISING AN OMEGA-3 FATTY ACID COMPOSITION AND AN SGLT2 INHIBITOR

This application claims the benefit under 35 U.S.C. §119 (e) of Application No. 62/055,055 filed on 25 Sep. 2014 and Application No. 62/075,471 filed on 5 Nov. 2014.

The present invention relates to methods for treating non-alcoholic fatty liver disease (NAFLD) and/or non-alcoholic steatohepatitis (NASH) with a combination of a sodium glucose co-transporter 2 (SGLT2) inhibitor and an omega-3-fatty acid composition (wherein the omega-3-fatty acid composition comprises one or more omega-3 fatty acids which may be present as free acids, esters, triglycerides, phospholipids or salts). The present invention also relates to methods of treating NAFLD and/or NASH where the SGLT2 inhibitor is dapagliflozin and/or the omega-3 fatty acid composition is provided as Epanova® (USAN=omega-3 carboxylic acids). The present invention further relates to combinations of Epanova® and SGLT-2 inhibitors. The present invention further relates to combinations of dapagliflozin with omega-3-fatty acid compositions. The present invention also relates to the specific combination of dapagliflozin and Epanova®.

NAFLD affects an estimated 15-40% of the general population (source Alimentary Pharmacol Ther, 2014, 39, 254-269), up to 85% in obese populations and 75% of Type 2 diabetes patients and encompasses a spectrum of diseases ranging from simple fatty liver (non-alcoholic fatty liver, NAFL) to NASH. Few studies have looked into the prevalence of NASH, although most indicate a prevalence of 3-7%, but a recent study based upon liver biopsy showed that the numbers could be higher than previously expected, 10.9% in a non-diabetes population and 22.2% in a diabetes cohort (Williams, Gastroenterology 2011; 140: 124-131). NASH can progress into fibrosis and cirrhosis of the liver and can therefore become a life-threatening disease. Furthermore, the risk of developing CV events or Hepatocellular Cancer is higher in patients with NASH. The whole spectrum of NAFLD has been associated with metabolic syndrome. There is increasing evidence showing that fibrosis development in patients with NASH is more prone in patients with poor glucose control and more severe insulin resistance (Moore J B. Non-alcoholic fatty liver disease: the hepatic consequence of obesity and the metabolic syndrome. Proc Nutr Soc 2010; 69: 211-20.) The definition of NAFLD is >5.56%, or more often >5.5%, liver fat content as determined by magnetic resonance spectroscopy (MRS) or magnetic resonance imaging (MRI).

Diagnosis of NASH is made from clinical and histopathological findings. The diagnosis of NASH requires, for example, that the subject has no significant alcohol consumption. The histopathological diagnosis is made by a trained pathologist and is generally made on the basis of a combination of four signs, which also measure the level of activity and the staging of the disease in the liver and together raise the probability of the patient suffering from NASH. These four signs are the degree of steatosis, degree of lobular inflammation, degree of ballooning (activity) and extent of fibrosis (stage). A diagnosis of definitive NASH over NAFL may also include other histopathological signs in a certain combination with steatosis, lobular inflammation and ballooning.

Steatosis, lobular inflammation and ballooning as mentioned above are measured as a combined NAS (NAFLD Activity Score), see Kleiner et al, Hepatology, 2006, 41(6), 1313-1321:

| Item | Score | Extent |
|---|---|---|
| Steatosis (from liver biopsy) | 0 | <5%* |
|  | 1 | 5-33% |
|  | 2 | >33-66% |
|  | 3 | >66% |
| Lobular Inflammation (from liver biopsy) | 0 | No foci |
|  | 1 | <2 foci/200x |
|  | 2 | 2-4 foci/200x |
|  | 3 | >4 foci/200x |
| Hepatocyte ballooning | 0 | None |
|  | 1 | Few balloon cells |
|  | 2 | Many cells/prominent ballooning |

*Percentage of hepatocytes containing fat droplets

As the NAS increases, the probability of having NASH increases such that in general, a NAS score of 5 gives about a 70% chance of having NASH, with a NAS score of 6 or more indicating almost a 100% probability of having NASH. Patients with a NAS score of 3 for example, could have NASH but the probability is low.

Fibrosis score is evaluated separately (by liver biopsy) to stage the disease but is not required for a diagnosis of NASH:

| Item | Score | Extent |
|---|---|---|
| Fibrosis | 0 | None |
|  | 1 | Perisinusoidal or periportal |
|  | 1A | Mild, zone 3, perisinusoidal |
|  | 1B | Moderate, zone 3, perisinusoidal |
|  | 1C | Portal/periportal |
|  | 2 | Perisinusoidal and portal/periportal |
|  | 3 | Bridging |
|  | 4 | Cirrhosis |

Various biomarkers of impaired liver function or liver damage are known in the art. These include transaminases (ALT and AST), alkaline phosphatase (ALP) (raised levels of which may indicate a bile duct disease), gamma-glutamyltransferase (GGT) and Cytokeratin (CK)18. Changes in one, two, three or all of these markers may be used as a biomarker for changes in disease state of the liver, potentially reducing or removing the need for liver biopsy for investigation of extent of disease.

Some studies have investigated the efficacy of treating patients with NAFLD and/or NASH with omega-3 fatty acid derivatives (effects on degree of steatosis is reviewed in Parker et al, J Hepatology, 2012, 56, 944-951) however additional clinical trials are needed to establish optimal doses, appropriate patient populations and quantify the benefit of this therapy.

SGLT2 is a member of a family of proteins that utilizes an electrochemical sodium gradient to transport glucose, against the sodium concentration gradient inside the cells. Different Na+/Glucose transporters are found in different tissues: SGLT1 is mainly found in intestinal mucosa in the small intestine and the S3 segment of the proximal tubule of the nephron in the kidney; and SGLT2 is mainly found in the 51 segment of the proximal tubule of the nephron in the kidney.

Diabetes Mellitus results from a mismatch between the demand and the supply of insulin resulting in increased glucose levels. Treatment of Diabetes Mellitus using SGLT2 inhibitors reduces plasma glucose by inhibiting the reabsorbtion of glucose in the kidneys, hence leading to an increase glucose excretion in the urine. Long term, and particularly, poorly controlled diabetes leads to a number of complications, for example of the cardiovascular system, some of which can become life threatening. One potential complication is increased triglycerides, such that many diabetic patients have triglyceride levels above recommended guidelines.

NAFLD patients are characterized by hyperinsulinemia and insulin resistance that is selective; reduced insulin action on hepatic glucose output but enhanced insulin action on de novo lipogenesis because of the hyperinsulinemia.

Tormeno et al (Expert Opinion Emerging Drugs, 2013, 18(3), 279-290) considers emerging drug treatments for NASH.

The effect of the SGLT-2 inhibitor ipragliflozin in treating abnormal accumulation of liver lipids has been investigated, see Katsuno et al, US2008/0045466, the disclosure of which is hereby incorporated by reference.

The effect of ipragliflozin on various parameters including hepatic steatosis in mice has been investigated (Eur J Pharmacology, 715 (2013), 246-255).

International patent application, publication number WO2014/142364 (Mochida Pharmaceuticals) discloses the use of EPA or derivatives (such as Epadel™) for the treatments of a fatty liver disease or disorder and includes a protocol for a Phase 2 clinical trial. Results from a phase 2 clinical trial with Epadel™ in the treatment of NASH were reported by Sanyal et al (Gastroenterology, 2014, 147; 377-384); Epadel™ failed to show any significant effect on hepatic steatosis or any histologic features of NASH in that trial.

US patent application US2014/0187633 described methods of treating or preventing nonalcoholic steatohepatitis and/or primary biliary cirrhosis using omega-3 fatty acids, particularly purified ethyl eicosapentaenoate.

Dapagliflozin has been shown to tend to reduce liver fat content in some studies in a diabetic population (Bolinder, J Clin Endocrinol Metab, 2012 March; 97(3):1020-31), however, the mechanism is not fully understood.

It is hypothesised that dapagliflozin may reduce liver fat via two mechanisms; negative energy balance as well as increased glucagon/insulin ratio, while Epanova® could reduce liver fat via decreased de novo lipogenesis and improved adipose tissue function that reduce fatty acid release, eventually also contributing to reduced body fat mass and therefore reduced flux of fatty acids to the liver. It is therefore hypothesised that a combination of dapagliflozin and Epanova® may result in a further reduction of liver fat than the drugs given alone by acting on distinct mechanisms involved in regulation of liver fat. Reduction in liver fat by the use of this combination comprises the treatment of non-alcoholic fatty liver disease (NAFLD) and/or non-alcoholic steatohepatitis (NASH) according to this invention.

Non-alcoholic fatty liver disease (NAFLD) is highly prevalent in patients with diabetes mellitus and increasing evidence suggests that patients with type 2 diabetes are at a particularly high risk for developing the progressive forms of NAFLD, non-alcoholic steatohepatitis (NASH) and associated advanced liver fibrosis. Pancreatic Exocrine Insufficiency, PEI, with impaired production and secretion of gastric enzymes such as amylase and lipases is also more common among patients with Diabetes Mellitus. The syndrome results in an impaired hydrolysis of fatty acids in the natural triglyceride or esterified form. Treatment of patients having PEI (as well as NAFLD and/or NASH) with a combination of the invention where the omega-3 fatty acid composition comprises omega-3 fatty acids in free acid form, may be more effective at reducing liver fat than treatment with a combination of the invention where the omega-3 fatty acid composition comprises omega-3 fatty acids in ester or triglyceride form (which require lipase in order to be hydrolysed to free fatty acid form for absorption).

We have investigated the effect of Epanova, dapagliflozin and the combination of the two components in two pre-clinical studies and a human clinical study, described in the Examples herein.

Although the two pre-clinical studies showed some beneficial effect of treatment with Epanova on NASH, in the two mouse models of NASH used dapagliflozin did not show any effect and any beneficial effect of the combination was attributed to the Epanova component. Surprisingly, it is believed the results of the Effect II human clinical trial (protocol described in the Examples hereinafter) will show a beneficial effect of the combination.

In previous human studies in diabetic patients, SGLT2 inhibitors have been shown to reduce body weight and increase insulin sensitivity, as well as showing a trend towards reduced liver fat content. In the NASH mouse studies included in the present application, no changes in body weight, glucose or insulin levels or liver fat were observed, however the NASH mouse models used were not diabetic, but were obese and insulin resistant. Therefore it is possible that the mouse models used in the Examples herein do not accurately model the effect of administration of SGLT-2 inhibitors in diabetic patients with respect to liver fat reduction, or other elements of the NAFLD activity score.

SUMMARY

In one aspect the present disclosure provides a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having, NASH.

In one aspect the omega-3 composition is provided as Epanova® or a bio-equivalent version thereof.

In another aspect, the SGLT-2 inhibitor is dapagliflozin.

In one aspect, the treatment comprises:
selecting a subject having, or suspected of having NASH on the basis of their NAFLD activity score;
administering an effective dose of an SGLT-2 inhibitor and an effective dose of an omega-3 fatty acid composition; and thereby improving the NAFLD Activity Score of said subject by at least 2 points, with no worsening of the subject's fibrosis stage score.

In another aspect, the treatment comprises:
selecting a subject having a NAFLD Activity Score greater than or equal to 5;
administering the combination; and thereby improving the NAFLD Activity Score of said subject by at least 2 points, with no worsening of the subject's fibrosis stage score.

In one aspect the patient has been diagnosed with Type II diabetes mellitus.

In a further aspect, there is provided a combination of an effective dose of Epanova® or a bioequivalent version thereof and an effective dose of dapagliflozin, for use as a medicament for reduction of liver fat in a subject who has been diagnosed with Type II diabetes mellitus and diagnosed as having raised liver fat (>5.5% as assessed by MRI or MRS). In one embodiment, the medicament also causes a reduction in plasma triglyceride level in the subject. In another embodiment, the medicament also causes raising of plasma EPA and/or DHA levels in the subject. In a further embodiment, the medicament also causes reduction of cell death and/or ballooning in the liver of the subject. In a further embodiment, the subject is also overweight (BMI>25).

In one aspect, there is provided a combination of an effective dose of Epanova® or a bioequivalent version thereof and an effective dose of dapagliflozin for use in the reduction of liver fat and the reduction of liver inflammation, in a subject in need thereof.

In another aspect, there is provided a combination of an effective dose of Epanova® or a bioequivalent version thereof and an effective dose of dapagliflozin for use in halting progression of liver fibrosis, in a subject in need thereof.

In a further aspect, there is provided a combination of an effective dose of Epanova® or a bioequivalent version thereof and an effective dose of dapagliflozin, in a subject who has been diagnosed with NAFLD or NASH, for use in halting progression of NAFLD and/or NASH comprising administering the combination and thereby causing a halt in progression of fibrosis of the subject's liver.

In a further aspect, there is provided a combination of an effective dose of Epanova® or a bioequivalent version thereof and an effective dose of dapagliflozin for use in the treatment of NASH, in a subject having, or suspected of having NASH, comprising administering the combination and thereby causing a reduction in body weight of the subject.

In a further aspect, there is provided a combination of an effective dose of Epanova® or a bioequivalent version thereof and an effective dose of dapagliflozin for use in the treatment of NASH, in a subject having, or suspected of having NASH, comprising administering the combination and thereby causing an increase in insulin sensitisation of the subject.

In a further aspect, there is provided a combination of Epanova® or a bioequivalent version thereof and dapagliflozin.

In one embodiment, 1 g, 2 g or 4 g of Epanova per day is used.

In another embodiment, 5 or 10 mg of dapagliflozin is used.

In one aspect, the present disclosure provides methods for treating NAFLD and/or NASH comprising administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts) to a warm-blooded animal in need of such treatment. In one embodiment of this aspect, the method is for treatment of NASH.

In a particular aspect, treatment with the omega-3 fatty acid composition and the SGLT-2 inhibitor is particularly effective at improving the subject's steatosis score, and so particularly effective at reducing liver fat.

In some embodiments, the subject shows unobstructed or normal excretion of bile, does not suffer from injury in the liver, does not exhibit liver dysfunction, shows normal levels of direct bilirubin and does not possess biliary tract disease or the subject possesses biliary tract disease in an early stage.

In some embodiments, the subject does not have a condition selected from the group consisting of alcoholic liver injury, drug-induced liver injury, chronic active hepatitis, cirrhosis and liver cancer.

In some aspects, the subject does not have a familial history of fatty liver disease.

In other aspects, the subject has one or more genetic polymorphisms associated with increased risk of fatty liver disease.

In other aspects, the subject has a familial history of fatty liver disease.

In one aspect, the humans to be treated with the above combinations of omega-3 fatty acid compositions and SGLT-2 inhibitors have been diagnosed as suffering from Type II diabetes (in addition to NAFLD and/or NASH). In another aspect, the humans to be treated with the above combinations have not been diagnosed as suffering from Type II diabetes. In a further aspect, the humans to be treated with the above combinations are those that do not exhibit symptoms of diabetes and have a plasma glucose level below 11.1 mmol/L, have a fasting plasma glucose level below 7 mmol/L; or have a two-hour plasma glucose level of below 11.1 mmol/L during an oral glucose tolerance test.

In one aspect, the humans to be treated with the above combinations of omega-3 fatty acid compositions and SGLT-2 inhibitors suffer from pancreatic exocrine insufficiency (in addition to NAFLD and/or NASH). In a further aspect, the humans to be treated suffer from pancreatic exocrine insufficiency and Type II diabetes (in addition to NAFLD and/or NASH). In some aspects, the patients to be treated are overweight, with a Body Mass Index (BMI) of >25.

In a further aspect, the present disclosure provides a combination of an SGLT-2 inhibitor with an omega-3 fatty acid composition (wherein the omega-3 fatty acid composition contains one or more omega-3 fatty acids which may be present as acids, esters, triglycerides, phospholipids or salts).

In a further aspect, there is provided a combination of an SGLT-2 inhibitor with an omega-3 fatty acid composition (wherein the omega-3 fatty acid composition contains one or more omega-3 fatty acids which may be present as acids, esters, triglycerides, phospholipids or salts), and wherein the omega-3 fatty acid composition comprises DHA.

In one aspect, there is provided a combination of an SGLT-2 inhibitor with an omega-3 fatty acid composition wherein the omega-3 fatty acid composition contains one or more omega-3 fatty acids in free acid form.

In one aspect, the combination of an SGLT-2 inhibitor with an omega-3 fatty acid composition reduces liver fat more than either component given alone.

In another aspect, the combination of an SGLT-2 inhibitor with an omega-3 fatty acid composition may reduce liver fat by an amount approximately equivalent to the sum of the effects of the individual components (so has an additive effect).

In another aspect, the combination of an SGLT-2 inhibitor with an omega-3 fatty acid composition may reduce liver fat more than the sum of the effects of each individual component given alone (so has a greater than additive effect).

Specific preferred embodiments of the present invention will become evident from the following more detailed description of certain preferred embodiments and the claims.

In one embodiment, the present invention provides methods wherein the warm-blooded animal is a human.

In one embodiment, the omega-3 fatty acid composition is in the form of an encapsulated oil.

BRIEF DESCRIPTION OF THE FIGURES

FIG. 1 shows the effects of Dapagliflozin (B), Epanova (C), Ipragliflozin (E), Canagliflozin (G) alone and combinations of Epanova with Dapagliflozin (D), Ipragliflozin (F) and Canagliflozin (H) compared with a the control group given vehicle (A) on NAFLD activity score.

FIG. 2 shows effects of Dapagliflozin (B), Epanova (C), Ipragliflozin (E), Canagliflozin (G) alone and combinations of Epanova with Dapagliflozin (D), Ipragliflozin (F) and Canagliflozin (H) compared with a the control group given vehicle (A) on fibrosis stage.

FIG. 3 shows effects of Epanova (Epa), Dapagliflozin (Dapa) and the combination of Epanova and Dapagliflozin (Epa+Dapa) on histological assessment of steatosis (A), inflammation (B), ballooning (C) and the sum of these assessments given as NAFLD activity score (D).

FIG. 4 shows effects of Epanova (Epa), Dapagliflozin (Dapa) and the combination of Epanova and Dapagliflozin (Epa+Dapa) on histological assessment of stage of fibrosis.

PANCREATIC EXOCRINE INSUFFICIENCY

The validation and increased use of faecal elastase-1 (FE-1) concentration (FEC) measured by pancreatic elastase-1 tests have allowed recent studies in larger populations to investigate the prevalence of pancreatic exocrine insufficiency (PEI). Faecal elastase-1 is a very stable protein secreted from the exocrine pancreas and found intact in faeces. The FE-1 test has a high predictive value and high sensitivity for PEI. A good correlation has been observed between FEC mass and duodenal lipase (r=0.84; p<0.001), amylase, trypsin, volume and bicarbonate output. It has been suggested that a FEC value of <100 µg/g or <200 µg/g is a sign of PEI. See Stevens et al, DigDisSci 2004; 49:1 405-11. Other methods of diagnosing PEI are known in the art and may also suitable used to diagnose patients suffering from PEI, as well as NAFLD and/or NASH, who may be suitable for treatment according to the present disclosure.

Omega-3 Fatty Acids

Pharmaceutical compositions rich in omega-3 polyunsaturated fatty acids (PUFAs) have been developed to treat a variety of clinical indications, including various disorders of blood lipids, including hypertriglyceridemia and mixed dyslipidemia.

Omega-3 (OM3) fatty acids are generally naturally derived mixtures from sources such as fish, which may then be subject to further processing, and will often be present in conjunction with other fatty acids such as omega-6 fatty acids. The exact composition of the fatty acid mixture may depend on the source of the acids and the extent and nature of the further processing. Typically, such mixtures are rich in eicosapentaenoic acid (C20:5 n-3) ("EPA," also known as timnodonic acid). Docosahexaenoic acid (C22:6 n-3) ("DHA," also known as cervonic acid) and/or docosapentaenoic acid (C22:5 n-3) ("DPA," also known as clupanodonic acid) may typically also be present in some proportion.

Several prescription omega-3 products have been approved for human use, for example the Food and Drug Administration (FDA)-approved omega-3 ethyl ester drugs. The US FDA first approved an omega-3 fatty acid ethyl ester mixture (Lovaza®, omega-3-acid ethyl esters, GlaxoSmithKline, Research Triangle Park, N.C.) as a dietary adjunct to reduce TG levels in adults with very high (≥500 mg/dL) TG levels in 2004. The active ingredient of Lovaza® comprises fatty acid ethyl esters (EEs), predominantly EPA-EE (approximately 465 mg/1 g capsule) and DHA-EE (approximately 375 mg/1 g capsule). Lovaza® has a recommended dose of 4 g/day.

More recently, a generic equivalent to Lovaza® by Teva Pharmaceuticals (Petah Tikva, Central District) as well as drugs with a similar EE mixture such as Omtryg® (omega-3-acid ethyl esters A, Trygg Pharmaceuticals, Oslo, Norway), have also been granted marketing authorization in various countries. Other trademarks may also be used for some of these products in various countries.

Reference herein to a "bio-equivalent version" of a composition is intended to refer to a version of the composition which has, or could be, granted marketing authorization by a regulatory body on the basis of being bio-equivalent to the composition. Pharmaceutical products are bioequivalent if they are pharmaceutically equivalent (same dosage form and route of administration for example) and their bioavailabilities (rate and extent of availability) after administration in the same molar dose are similar to such a degree that their effects, with respect to both efficacy and safety, can be expected to be essentially the same.

For convenience herein, omega-3 fatty acid compositions comprising a mixture of omega-3 fatty acids substantially in the form of ethyl esters will be referred to as OM3-EE compositions (which may be abbreviated to OM3-EE).

In certain embodiments, the omega-3 fatty acid composition comprises EPA, substantially in ester form, and DHA, substantially in ester form. The omega-3 pharmaceutical composition may comprise EPA, substantially in ethyl ester form, in an amount of about 35 to about 60% by weight and DHA, substantially in ethyl ester form, in an amount of about 25 to about 50% by weight.

Vascepa® (INN icosapent ethyl, Amarin Pharma Inc., Bedminster, N.J.), comprises purified EPA-EE and has a recommended dose of 4 g/day. Epadel® is a formulation of EPA-EE which is approved in Japan and marketed by Mochida Pharmaceuticals.

However, EPA-EE and DHA-EE require hydrolysis by pancreatic lipase prior to intestinal absorption, thus need to be taken with food for optimal absorption. The release of pancreatic lipases is stimulated by dietary fat, and because some patients with severe hypertriglyceridemia will be advised to adhere to a low-fat diet as part of their treatment plan, there has been considerable interest in an OM3 fatty acid drug with enhanced bioavailability that is not subject to these dietary constraints.

Epanova® (USAN omega-3 carboxylic acids) was approved by the FDA in May 2014 as 2 g or 4 g dose as an adjunct to diet to reduce triglyceride (TG) levels in adult patients with severe (>500 mg/dL) hypertriglyceridemia and comprises a mixture of free fatty acids (FFA), with EPA-FFA and DHA-FFA as the most abundant omega-3 species; the active ingredient is encapsulated in a soft gelatin capsule coated with polyacrylate material. The manufacturing of this free fatty acid product requires an additional step compared with that of the available OM3-EE drugs. This consists of the hydrolysis and distillation of the EE to produce the omega-3 free fatty acids.

The composition used in Epanova® contains EPA and DHA in concentrations of approximately 50-60 wt % of fatty acids and 15-25 wt % of fatty acids, respectively. Epanova® contains approximately 75 wt % EPA+DHA per 1 gram capsule and is a complex mixture comprising a plurality of species of omega-3-FAs and a plurality of species of omega-6-FAs, each present substantially in free acid form. One of these other omega-3 FA species is DPA which is present in about 1-8 wt % fatty acids. Examples of the free fatty acid compositions used for Epanova® are described in WO2013/103902, such as in Example 7 therein, and such as Table 10 therein, which is reproduced for convenience as Table 1 below.

In particular embodiments, the omega-3 fatty acid composition comprises EPA, substantially in free acid form, DHA, substantially in free acid form and docosapentaenoic acid (DPA) substantially in free acid form. The omega-3 fatty acid composition may comprise EPA in an amount of at least 50 wt % of fatty acids, DHA in an amount of at least 15 wt % of fatty acids and DPA in an amount of at least 1 wt % of fatty acids, wherein each of EPA, DHA and DPA are substantially in free acid form. The omega-3 fatty acid composition may comprise EPA in an amount of about 50 wt % to about 60 wt % of fatty acids, DHA in an amount of about 17 wt % to about 23 wt % of fatty acids and DPA in an amount of about 1 wt % to about 8 wt % of fatty acids, wherein each of EPA, DHA and DPA are substantially in free acid form. In particular embodiments, DPA is present in an amount of at least about 1.5 wt % of fatty acids, such as at least about 2 wt % of fatty acids, such as at least about 2.5 wt % of fatty acids, such as at least about 3 wt % of fatty acids, such as about 3.5 wt % of fatty acids, such as at least about 4 wt % of fatty acids, such as at least about 4.5 wt % of fatty acids.

In one aspect, the omega-3 fatty acids in the omega-3 fatty acid composition for use in the present invention are in free fatty acid form. Suitable omega-3 free fatty acid mixtures for use in the present invention are disclosed in WO2013/103902, the contents of which are hereby incorporated by reference. In one embodiment of this aspect, the free fatty acid composition is provided as Epanova® or a bio-equivalent version thereof. In another embodiment of this aspect, the free fatty acid composition is provided as Epanova®.

It will be understood that reference herein to Epanova® may be substituted by its USAN name, omega-3 carboxylic acids. In other embodiments, reference to Epanova® may be substituted by the following description:

a unit dosage form containing a polyunsaturated fatty acid composition comprising:
EPA in a weight percent amount of 50% to 60%;
DHA in a weight percent amount of 17% to 23%;
DPA in a weight percent amount of 1% to 8%; wherein a least 90% by weight of the polyunsaturated fatty acid in the composition is present in free acid form.

For convenience, omega-3 fatty acid compositions containing a mixture of omega-3 fatty acids substantially in free fatty acid form (carboxylic acid form), such as that provided in Epanova®, will be referred to herein as OM3-CA compositions, which may be abbreviated to OM3-CA.

It will be understood that the term "compositions" used herein is intended to refer to the (mixture of) oils which is the active pharmaceutical ingredient. So reference to an OM3-CA composition is intended to refer to an oil mixture containing omega-3 fatty acids in free fatty acid form. Such compositions may be provided in finished pharmaceutical dosage form, such as an approved pharmaceutical product, such as Epanova®. It will be further understood that reference to a "product" is intended to refer to the finished pharmaceutical dosage form, containing the active ingredient. So reference to an OM3-CA product, such as Epanova®, refers to the encapsulated oil composition. Equivalent wording is used for ethyl ester containing oil compositions and their respective approved products.

In one aspect, the omega-3 fatty acid composition for use in the present invention is an OM3-EE composition. In one embodiment of this aspect, the OM3-EE composition is provided as Lovaza®. In a further embodiment, the OM3-EE composition is provided as Omtryg®. In further embodiments, the OM3-EE composition is provided in any product which has been granted marketing authorization by a regulatory body on the basis of being bio-equivalent to any of the OM3-EE drugs hereinbefore.

In another embodiment, the omega-3 fatty acid composition is provided as Vascepa® or a bio-equivalent version thereof. In another embodiment, the omega-3 fatty acid composition is provided as Vascepa®.

In one aspect, the omega-3 fatty acid composition comprises DHA (in free acid, ester, triglyceride or phospholipid form) and is, for example, provided as Lovaza® or Epanova®, or bio-equivalent versions thereof

TABLE 1

| | | \multicolumn{10}{c}{Final (free acid) API Batches} |
|---|---|---|---|---|---|---|---|---|---|---|---|
| | | Batch 1 | Batch 2 | Batch 3 | Batch 4 | Batch 5 | Batch 6 | Batch 7 | Batch 8 | Batch 9 | Batch 10 |
| | API Batch # | 36355 | 36395 | 37225 | 37289 | 38151 | 38154 | 38157 | 38300 | 38303 | 38306 |
| | Intermediate Batch # | 1 | 1 | 2 | 3 | 4 | 4 | 5 | 7 | 8 | 6 |
| Identity | Common name | area % | area % | area % | area % | area % | area % | area % | area % | area % | area % |
| C18:2(n-6) | Linoleic acid | 0.55 | 0.49 | 0.59 | 0.55 | 0.60 | 0.61 | 0.78 | 0.62 | 0.53 | 0.72 |
| C18:3(n-6) | Gamma-linolenic acid | 0.15 | 0.14 | 0.12 | 0.12 | 0.17 | 0.16 | 0.16 | 0.22 | 0.15 | 0.15 |
| C18:3(n-3) | α-Linolenic acid | 0.39 | 0.34 | 0.38 | 0.37 | 0.45 | 0.45 | 0.55 | 0.41 | 0.44 | 0.50 |
| C18:4(n-3) | Moroctic acid | 1.70 | 1.67 | 1.16 | 1.26 | 1.37 | 1.37 | 1.87 | 1.65 | 1.77 | 1.81 |
| C20:2(n-6) | Eicosadienoic acid | 0.10 | 0.13 | 0.12 | 0.09 | 0.10 | 0.10 | 0.27 | 0.12 | 0.11 | 0.12 |

TABLE 1-continued

Final (free acid) API Batches

| | | Batch 1 | Batch 2 | Batch 3 | Batch 4 | Batch 5 | Batch 6 | Batch 7 | Batch 8 | Batch 9 | Batch 10 |
|---|---|---|---|---|---|---|---|---|---|---|---|
| C20:3(n-6) | Dihomo-gamma-linolenic acid | 0.35 | 0.39 | 0.45 | 0.42 | 0.42 | 0.45 | 0.52 | 0.51 | 0.42 | 0.51 |
| C20:4(n-6) | Arachidonic acid | 2.43 | 2.45 | 2.84 | 2.86 | 3.50 | 3.50 | 3.64 | 4.02 | 2.57 | 3.60 |
| C20:3(n-3) | Eicosatrienoic acid | 0.15 | 0.25 | 0.22 | 0.16 | 0.20 | 0.17 | 0.25 | 0.18 | 0.17 | 0.23 |
| C20:4(n-3) | Eicosatetraenoic acid | 2.18 | 2.02 | 2.11 | 2.09 | 1.96 | 1.90 | 2.64 | 2.13 | 2.34 | 2.54 |
| C20:5(n-3) | EPA | 57.25 | 57.64 | 55.81 | 57.08 | 56.25 | 56.38 | 56.88 | 56.30 | 56.72 | 57.15 |
| C21:5(n-3) | Heneicosapentaenoic acid | 2.79 | 2.75 | 2.72 | 2.78 | 2.68 | 2.60 | 2.15 | 2.57 | 2.88 | 2.18 |
| C22:5(n-6) | Docosapentaenoic acid | 0.20 | 0.17 | 0.72 | 0.71 | 0.61 | 0.62 | 0.66 | 0.63 | 0.71 | 0.66 |
| C22:5(n-3) | DPA | 6.23 | 6.22 | 5.46 | 5.49 | 6.12 | 5.97 | 3.41 | 5.15 | 5.59 | 3.43 |
| C22:6(n-3) | DHA | 19.58 | 19.65 | 19.45 | 20.00 | 19.16 | 18.79 | 20.60 | 20.10 | 20.97 | 21.01 |

In another aspect, the omega-3 fatty acids in the omega-3 fatty acid composition are substantially present as triglycerides.

In another aspect, the omega-3 fatty acids in the omega-3 fatty acid composition are substantially present as phospholipids.

In another aspect, the omega-3 fatty acids in the omega-3 fatty acid composition are substantially present as salts.

In the above aspects, the omega-3 fatty acids are described as being substantially in a particular form, it will be understood to mean that the omega-3 fatty acids are at least 70%, such as at least 80%, such as at least 90%, such as at least 95%, such as at least 98% in the specified form.

The omega-3 fatty acid composition may comprise one or more excipients or diluents. For example alpha-tocopherol may be present.

In another aspect, the omega-3 fatty acid composition is usefully packaged in unit dosage forms for oral administration.

In particular embodiments, the dosage form comprising an omega-3 fatty acid composition is a capsule. In certain embodiments, the dosage form is a hard gelatin capsule. In other embodiments, the dosage form is a soft gelatin capsule.

In various embodiments, the capsule comprises Type A gelatin. In certain embodiments, the capsule comprises Type B gelatin. In some embodiments, the capsule comprises both Type A and Type B gelatin. Sources of collagen for the production of either type A or type B gelatin include, but are not limited to, cows, pigs and fish.

In various embodiments, the capsule is a soft gelatin capsule in which at least about 1% (w/w) of the gelatin is Type A gelatin. In certain embodiments, at least about 2% (w/w), 3% (w/w), 4%, (w/w), 5% (w/w), 6% (w/w), 7% (w/w), 8% (w/w), 9% (w/w), or at least about 10% (w/w) of the gelatin is Type A gelatin. In selected embodiments, at least about 15% (w/w), 20% (w/w), 25% (w/w), 30% (w/w), 35% (w/w), 40% (w/w), 45% (w/w), even at least about 50% (w/w), 55% (w/w), 60% (w/w), 65% (w/w), 70% (w/w), 75% (w/w), 80% (w/w), 85% (w/w), 90% (w/w), 95% or more of the gelatin is Type A gelatin.

In particular embodiments, the gelatin of the capsule consists essentially of type A gelatin.

In certain embodiments, the Type A gelatin is porcine Type A gelatin.

In some embodiments, the capsule is a reduced cross-linked gelatin capsule, such as those described in U.S. Pat. No. 7,485,323, incorporated herein by reference in its entirety. In a variety of embodiments, capsules are made from substances that are not animal by-products, such as alginate, agar-agar, carrageenan, pectin, konjak, guar gum, food starch, modified corn starch, potato starch, and tapioca. Non-animal sources of materials that can be used to make capsules are described in U.S. Patent Publication No. 2011/0117180, incorporated herein by reference. In some embodiments, Vegicaps® Capsules (Catalent) are used. In some embodiment the capsule can be a combination of non-animal product such as alginate and type A or B gelatin.

In certain embodiments, the capsule comprises a chemically-modified gelatin. In various embodiments, the chemically-modified gelatin is a succinylated gelatin.

In certain capsular oral unit dosage form embodiments, the capsule is uncoated. In a variety of embodiments, the capsule is coated.

In certain coated capsule embodiments, the capsule is coated with a coating on the exterior of the capsule that causes the encapsulated omega-3 fatty acid composition to be released in a time-dependent manner. In various embodiments, release of the omega-3 fatty acid composition is delayed for at least 15 minutes after ingestion. In particular embodiments, release of the omega-3 fatty acid composition is delayed for at least 30 minutes after ingestion. In other embodiments, release of the fatty acid composition is delayed for about 30 minutes to about 60 minutes after ingestion. In various coated embodiments, the coating is selected from cellulose acetate trimellitate, cellulose acetate phthalate and poly(ethylacrylate-methylacrylate). In some embodiments, such as in Epanova®, the coating is a neutral polyacrylate such as poly(ethylacrylatemethylmethacrylate), such as Eudragit NE 30-D (Evonik Industries AG), which has an average molecular weight of about 800,000). In other embodiments, the coating is another of the Eudragit-type of coatings (Evonik Industries AG), such as a sustained release coating, such as Eudragit RL 100, RL PO, RL 30 D, RL 12-5, RS100, RS PO, RS 30D, RS 12-5, NE 40 D, or NM 30 D.

In certain embodiments, capsules are coated as described in U.S. Pat. Nos. 5,792,795 and 5,948,818, the disclosures of which are incorporated herein by reference. In certain embodiments, such as in Epanova®, the dosage form is a coated soft gelatin capsule comprising porcine type A gelatin, as described in U.S. Pat. No. 7,960,370, incorporated herein by reference.

In various embodiments, the oral unit dosage form contains from about 100 mg to about 2000 mg of the omega-3 fatty acid composition described herein. In some embodiments, the oral dosage form contains about 250 mg of the omega-3 fatty acid composition. In some embodiments, the oral dosage form contains about 500 mg of the omega-3 fatty acid composition. In certain embodiments, the oral dosage form contains about 750 mg of the omega-3 fatty acid composition. In some embodiments, the oral dosage form contains about 1000 mg of the omega-3 fatty acid composition. In other embodiments, the oral dosage form contains about 1500 mg of the omega-3 fatty acid composition. In certain embodiments, the unit dosage form contains nonintegral weight amounts of omega-3 fatty acid, typically between 100 mg and 2000 mg.

In some embodiments, the dosage form encapsulates PUFAs in an amount of about 50 mg to about 2000 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg.

In further embodiments, the omega-3 fatty acid composition is provided in a plurality of small millicapsules, each containing a small amount of the omega-3 fatty acid composition (for example 5, 10, 15, 20, 25, 30, 40, 50, 75, or 100 mg±about 5 or 10%, in particular about 25 mg±about 5 or 10%), and packaged (for example in a sachet) such that a total dose of, for example, one gram or two grams of omega-3 fatty acid composition is provided as a unit dosage form. Conveniently, such millicapsules are approximately seamless millicapsules comprising gelatins and, optionally, coatings as described hereinbefore for larger capsules. The term "millicapsule" will be understood to mean a capsule with dimensions of generally less than 10 mm. For example, in some embodiments, the millicapsules may be spherical or approximately spherical in shape and include a diameter from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In other embodiments, millicapsules are ellipsoidal or approximately ellipsoidal in shape and include semi-principle axes (i.e., semi-major axis and semi-minor axis of the corresponding ellipses) of millimeter dimensions. For example, millicapsules may be ellipsoidal in shape and include semi-principle axes independently selected from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In some embodiments, the millicapsules include semi-principle axes independently selected from about 1, 2, 3, 4, 5, 6, or 7 mm±about 0.1, 0.2, 0.3, or 0.5 mm. In certain embodiments where the millicapsules are ellipsoidal in shape, the millicapsules have a circular or approximately circular cross section (e.g., have two substantially equal semi-principle axes). In such embodiments, the diameter of the circular cross section may be selected from about 10 to about 0.1 mm, such as about 8 to about 0.5 mm, such as about 7 to about 1 mm, such as about 6 to about 2 mm, such as about 5 to about 3 mm, such as about 4 mm±about 0.1, 0.2, 0.3, or 0.5 mm. In some embodiments, the diameter of the circular cross section is about 1, 2, 3, 4, 5, 6, or 7 mm±about 0.1, 0.2, 0.3, or 0.5 mm.

In various embodiments, the pharmaceutical composition present in the unit dosage form is stable at room temperature (about 23° C. to 27° C., or about 25° C.) and about 60% relative humidity for a period of at least six months, at least one year, or at least two years.

SGLT2 Inhibitors

The SGLT2 inhibitors employed in the invention are most preferably selective for SGLT2 relative to SGLT1. High selectivity for SGLT2, as is the case with dapagliflozin, is advantageous for use in the current invention because it avoids the unpredictable effects of intestinal SGLT1 inhibition.

Selectivity for SGLT2 of a given inhibitor can be determined by comparing the $EC_{50}$ values measured in an SGLT1 and SGLT2 assay. Briefly, Human SGLT1 (hSGLT1) and human SGLT2 (hSGLT2) full-length cDNA sequences are cloned by PCR using MARATHON READY™ human kidney cDNA (Clontech, Mountain View, Calif.), with primers designed from published sequences (Genbank accession numbers NM_003041 and NM_000343). The hSGLT1 and hSGLT2 sequences are cloned into pIRESneo vector (Clontech, Mountain View, Calif.) for mammalian expression and are stably transfected into Chinese hamster ovary (CHO) cells. SGLT-expressing clones are selected based on resistance to G418 antibiotic (GENETICIN®, Invitrogen, Carlsbad, Calif.) and activity in the $^{14}C$-α-methyl-D-glucopyranoside ($^{14}C$-AMG) uptake assay.

Cells expressing hSGLT1 or hSGLT2 are maintained using standard cell culture techniques. Assays for sodium-dependent glucose transport in 96-well plates are initiated by adding 100 μl/well of protein-free assay buffer containing sodium (Hepes/Tris pH 7.4, 137 mM NaCl, 5.4 mM KCl, 2.8 mM $CaCl_2$, 1.2 mM $MgSO_4$), 10 μM $^{14}C$-AMG and inhibitor or dimethyl sulfoxide (DMSO) vehicle, and plates are incubated for 2 h at 37° C. Sodium-dependent $^{14}C$-AMG uptake is calculated by subtracting the counts per minute (CPM) observed under sodium-free uptake conditions from the counts observed under sodium-containing conditions Inhibitors are assayed at various concentrations in triplicate in the presence of sodium, and the percent inhibition is calculated by comparing CPM in inhibitor-containing wells with CPM in wells containing only DMSO vehicle. Phlorizin, a known non-selective SGLT inhibitor, is evaluated in parallel in every assay. A dose-response curve is fitted to an empirical four-parameter model using XL Fit (IDBS, Guilford, UK) to determine the inhibitor concentration at half-maximal response ($EC_{50}$). SGLT2 selectivity is represented as a ratio of $EC_{50}$ in favor of SGLT2. An SGLT2 inhibitor with an $EC_{50}$ selective ratio of at least 10, and more preferably at least 100, in favor of SGLT2 is suitable for use in the instant invention.

SGLT2 inhibitors suitable for use in accordance with the invention comprise C-arylglucosides or O-arylglucosides. C-arylglucosides and O-arylglucosides are effective in treating diabetes. See U.S. Pat. No. 6,774,112, which is incorporated herein by reference in its entirety.

Examples of C-arylglucoside (also referred to as C-glucosides) SGLT2 inhibitors which can be employed in the methods of the invention, include, but are not limited to, the following:

1) C-aryl glucosides as disclosed in U.S. Pat. Nos. 6,515,117 and 6,414,126, the disclosures of which are incorporated herein by reference in their entirety for any purpose;

2) C-aryl glucosides as described in U.S. patent application Ser. No. 11/233,617 (U.S. Patent Application Publication No. 2006/0063722 A1), the disclosure of which is incorporated herein by reference in its entirety;

3) C-aryl glucosides described in U.S. Pat. No. 6,774,112, the disclosure of which is incorporated herein by reference in its entirety;

4) Glucopyranosyl-substituted benzene derivatives as disclosed in U.S. Patent Application Publication No. 2005/0209166, the disclosure of which is incorporated herein by reference in its entirety; and 5) D-pyranosyl-substituted phenyl compounds as disclosed in U.S. Patent Application Publication No. S 2006/0074031, the disclosure of which is incorporated herein by reference in its entirety.

Examples of O-glucoside SGLT2 inhibitors which can be employed in the methods of the invention include, but are not limited to, those described in the following:

1) 5-Thio-β-D-glucopyranoside as disclosed in U.S. Patent Application Publication No. 2006/0194809, the disclosure of which is incorporated by reference in its entirety for any purpose;

2) Glucopyranyloxybenzene derivatives as disclosed in WO 03/01180, the disclosure of which is incorporated by reference in its entirety for any purpose;

3) Pyrazole derivatives as disclosed in U.S. Pat. No. 6,908,905, the disclosure of which is incorporated herein by reference for any purpose; and 4) Pyrazole compounds as disclosed in U.S. Pat. No. 6,815,428, the disclosure of which is incorporated herein by reference for any purpose.

Other disclosures and publications disclosing SGLT2 inhibitors that can be employed in the methods of the invention are as follows: K. Tsujihara et al., *Chem. Pharm. Bull.*, 44:1174-1180 (1996); M. Hongu et al., *Chem. Pharm. Bull.*, 46:22-33 (1998); M. Hongu et al., *Chem. Pharm. Bull.*, 46:1545-1555 (1998); and A. Oku et al., *Diabetes*, 48:1794-1800 (1999) and JP 10245391 (Dainippon).

In a preferred aspect, the invention provides SGLT2 inhibitors for use in the methods of the invention that are disclosed in U.S. Pat. Nos. 6,414,126 and 6,515,117, more preferably the SGLT2 inhibitor is compound I or dapagliflozin

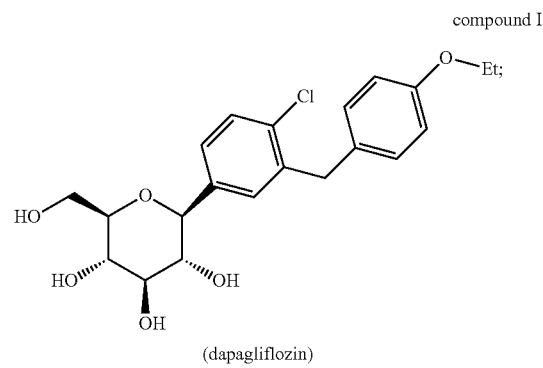 [SMILES: CCOc1ccc(Cc2cc([C@@H]3O[C@H](CO)[C@@H](O)[C@H](O)[C@H]3O)ccc2Cl)cc1]

(dapagliflozin)

or a pharmaceutically acceptable salt thereof, all stereoisomers thereof, or a prodrug ester thereof.

In another preferred aspect, the invention provides crystalline forms of compound I including the crystalline forms disclosed in U.S. Patent Application Publication No. 2008/0004336, the disclosure of which is incorporated herein by reference in its entirety for any purpose. Most preferred crystalline forms for use in the methods of the present invention are dapagliflozin (S) propylene glycol hydrate and dapagliflozin (R) propylene glycol hydrate.

Additional SGLT2 inhibitors that may be employed in the present invention include canagliflozin (Johnson & Johnson/Mitsubishi Tanabe Pharma); remogliflozin etabonate (Islet Sciences, Kissei Pharmaceuticals Co.); ipragliflozin (Astellas/Kotobuki); empagliflozin (Boehringer Ingelheim); BI-44847 (Boehringer Ingelheim); TS-071 (Taisho Pharmaceutical); tofogliflozin (Roche/Chugai Pharmaceutical); LX-4211 (Lexicon Pharmaceuticals); DSP-3235 (GlaxoSmithKline/Dainippon Sumitomo); ISIS-SGLT2Rx (Isis Pharmaceuticals); and YM543 (Astellas Pharma Inc). A further SGLT-2 inhibitor is ertugliflozin (Pfizer and Merck).

Various forms of prodrugs are known in the art. For examples of such prodrug derivatives, see:

a) Design of Prodrugs, edited by H. Bundgaard, (Elsevier, 1985) and Methods in Enzymology, Vol. 42, p. 309-396, edited by K. Widder, et al. (Academic Press, 1985);

b) A Textbook of Drug Design and Development, edited by Krogsgaard-Larsen and H. Bundgaard, Chapter 5 "Design and Application of Prodrugs", by H. Bundgaard p. 113-191 (1991);

c) H. Bundgaard, Advanced Drug Delivery Reviews, 8, 1-38 (1992);

d) H. Bundgaard, et al., Journal of Pharmaceutical Sciences, 77, 285 (1988); and e) N. Kakeya, et al., Chem Pharm Bull, 32, 692 (1984).

Examples of such prodrugs are in vivo cleavable esters of a compound of the invention. An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include (1-6C)alkyl esters, for example methyl or ethyl; (1-6C)alkoxymethyl esters, for example methoxymethyl; (1-6C)alkanoyloxymethyl esters, for example pivaloyloxymethyl; phthalidyl esters; (3-8C)cycloalkoxycarbonyloxy(1-6C)alkyl esters, for example 1-cyclohexylcarbonyloxyethyl; 1,3-dioxolan-2-ylmethyl esters, for example 5-methyl-1,3-dioxolan-2-ylmethyl; (1-6C)alkoxycarbonyloxyethyl esters, for example 1-methoxycarbonyloxyethyl; aminocarbonylmethyl esters and mono- or di-N-((1-6C)alkyl) versions thereof, for example N,N-dimethylaminocarbonylmethyl esters and N-ethylaminocarbonylmethyl esters; and may be formed at any carboxy group in the compounds of this invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include (1-6C)alkanoyl esters, for example acetyl esters; and benzoyl esters wherein the phenyl group may be substituted with aminomethyl or N-substituted mono- or di-(1-6C)alkyl aminomethyl, for example 4-aminomethylbenzoyl esters and 4-N,N-dimethylaminomethylbenzoyl esters.

The SGLT2 inhibitors employed in accordance with the invention can be administered to various mammalian species, such as dogs, cats, cattle, humans, etc., in need of treatment. These agents can be administered systemically, such as orally or parenterally.

The SGLT2 inhibitors utilized in the present invention are conveniently administered as pharmaceutical compositions that comprise the compounds formulated together with one or more pharmaceutically acceptable carriers. The pharmaceutical compositions can be specially formulated for oral administration in solid or liquid form, for parenteral injection or for rectal administration. The term "parenterally," as used herein, refers to modes of administration which include intravenous, intramuscular, intraperitoneal, intrasternal, subcutaneous and intraarticular injection and infusion.

The SGLT2 inhibitors are conveniently incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

Pharmaceutical compositions for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservative, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

Injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound is mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

Solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The SGLT2 inhibitors can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, an oral composition may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

The dose administered is adjusted according to the age, weight, and condition of the patient, as well as the route of administration, dosage form and regimen, and the desired result. In general, the dosage forms described above can be administered containing amounts of SGLT2 inhibitor of from about 1 to about 1000 mg per day, preferably from about 2 to about 400 mg per day, more preferably 2.5 to about 75 mg/day, and even more preferably from 2.5 to about 50 mg/day. In one aspect 5 or 10 mg/day are used.

The dosage forms can be administered in single doses or in divided doses of one to four times daily.

Unless otherwise indicated, dosages and formulations for SGLT2 inhibitors, used in the methods set forth herein are disclosed in the various patents and applications discussed throughout the application, which are incorporated herein in their entireties.

It will be recognized by one of skill in the art that the amount of drug required for therapeutic effect on administration will, of course, vary with the agent chosen, the nature and severity of the condition and the mammal undergoing treatment, and is ultimately at the discretion of the physician. Furthermore, the optimal quantity and spacing of individual dosages of a drug will be determined by the nature and extent of the therapeutic effects desired, the form, route and site of administration, the particular patient being treated and that such optima can be determined by conventional techniques. It will also be appreciated that the optimal course of treatment, for example, the number of doses given, can be ascertained by those skilled in the art using conventional course of treatment determination tests.

SGLT2 inhibitor activity of the compounds useful in the present invention can be determined by use of an assay system as set out below.

Assay for SGLT2 Activity

The mRNA sequence for human SGLT2 is cloned by reverse-transcription and amplification from human kidney mRNA, using standard molecular biology techniques. The cDNA sequence is stably transfected into CHO cells, and clones are assayed for SGLT2 activity essentially as described in Ryan et al., 1994, "HK-2: an immortalized proximal tubule epithelial cell line from normal adult human kidney," *Kidney International* 45:48-57. Evaluation of inhibition of SGLT2 activity in a clonally selected cell line is performed essentially as described in Ryan et al., with the following modifications. Cells are grown in 96-well plates for 2-4 days to 75,000 or 30,000 cells per well in F-12 nutrient mixture (Ham's F-12; GIBCO, Long Island, N.Y.), 10% fetal bovine serum, 300 µg/ml Geneticin and penicillin-streptomycin. At confluence, cells are washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells then are incubated with 10 µM [$^{14}$C]AMG, and 10 µM inhibitor (final DMSO=0.5%) in 10 mM Hepes/Tris, pH 7.4, 137 mM NaCl, 5.4 mM KCl, 2.8 mM $CaCl_2$, 1.2 mM $MgSO_4$ at 37° C. for 1.5 hr. Uptake assays are quenched with ice cold 1×PBS containing 0.5 mM phlorizin, and cells are then lysed with 0.1% NaOH. After addition of MicroScint scintillation fluid, the cells are allowed to shake for 1 hour, and then [$^{14}$C] AMG is quantified on a TopCount scintillation counter. Controls are performed with and without NaCl. For determination of $EC_{50}$ values, 10 inhibitor concentrations are used over 2 log intervals in the appropriate response range, and triplicate plates are averaged across plates. Ryan et al., Id.

Combination of Omega-3 Fatty Acids and SGLT-2 Inhibitors.

In one aspect, there is provided a combination of an SGLT-2 inhibitor and an omega-3 fatty acid composition (wherein the omega-3 fatty acid composition comprises one or more omega-3 fatty acids which may be present as acids, esters, triglycerides, phospholipids or salts). In one embodiment, the SLGT-2 inhibitor is selected from the group consisting of dapagliflozin, canagliflozin, remogliflozin etabonate, ipragliflozin, empagliflozin, BI-44847, TS-071, tofogliflozin, LX-4211, DSP-3235, ISIS-SGLT2Rx and YM543. In another embodiment, the SLGT-2 inhibitor is selected from the group consisting of dapagliflozin, canagliflozin, remogliflozin etabonate, ipragliflozin, empagliflozin, BI-44847, TS-071, tofogliflozin, LX-4211, DSP-3235, ISIS-SGLT2Rx, YM543 and ertugliflozin. In another embodiment, the SGLT-2 inhibitor is selected from the group consisting of dapagliflozin, canagliflozin, remogliflozin etabonate, ipragliflozin and empagliflozin. In another embodiment, the SGLT-2 inhibitor is selected from the group consisting of dapagliflozin, canagliflozin, and ipragliflozin. In another embodiment, the SGLT-2 inhibitor is dapagliflozin. In one embodiment, the omega-3 fatty acid composition comprises one or more omega-3 fatty acids which may be present as acids, esters, phospholipids or salts. In another embodiment, the omega-3 fatty acid composition comprises one or more omega-3 fatty acids which may be present as acids or esters. In another embodiment, the omega-3 fatty acid composition comprises one or more omega-3 carboxylic acids; in one embodiment, the omega-3 carboxylic acid composition is provided as Epanova®. In another aspect, the omega-3 fatty acid composition comprises a mixture of omega-3 fatty acid esters, such as ethyl esters. In another aspect, the omega-3 fatty acid composition comprises highly purified EPA-EE (such as >90% EPA-EE by weight, such as >95% EPA-EE, such as at least 98% EPA-EE). In one aspect, the omega-3 fatty acid composition is provided as Lovaza®, Vascepa® or Omtryg® or a bioequivalent version of any of these. In one aspect, the omega-3 fatty acid composition is provided as Lovaza® or a bioequivalent version thereof. In one aspect, the omega-3 fatty acid composition is provided as Vascepa® or a bioequivalent version thereof.

References herein to remogliflozin etabonate should be understood to apply to any other pro-drugs, or remogliflozin itself, unless the context demands otherwise.

It will be understood that when an omega-3 fatty acid composition is described herein as being in the form of free carboxylic acids, or as ethyl esters, this is intended to mean that this is the predominant form in the composition and does not preclude a minor proportion of the composition being in another form, such as carboxylic acid being present in predominantly ethyl ester composition, or triglyceride forms being present in either carboxylic acid or ethyl ester compositions.

In a further aspect, there is provided a combination of an SGLT-2 inhibitor with an OM3-CA product, such as Epanova®.

In a further aspect, there is provided a combination of an SGLT-2 inhibitor selected from dapagliflozin, canagliflozin, remogliflozin etabonate, ipragliflozin and empagliflozin with an OM3-CA product, such as Epanova®.

In a further aspect, there is provided a combination of dapagliflozin with an OM3-CA product, such as Epanova®.

In a further aspect, there is provided a combination of an SGLT-2 inhibitor with an OM3-EE product, such as Lovaza®, and Omtryg® or a bioequivalent version of any of these.

In a further aspect, there is provided a combination of an SGLT-2 inhibitor with an icosapent ethyl product, such as Vascepa®.

In a further aspect, there is provided a combination of an SGLT-2 inhibitor selected from dapagliflozin, canagliflozin, remogliflozin etabonate, ipragliflozin and empagliflozin with an OM3-EE product, such as Lovaza®, and Omtryg® or a bioequivalent version of any of these.

In a further aspect, there is provided a combination of an SGLT-2 inhibitor selected from dapagliflozin, canagliflozin, remogliflozin etabonate, ipragliflozin and empagliflozin with an icosapent ethyl product, such as Vascepa®.

In a further aspect, there is provided a combination of dapagliflozin with an OM3-EE product, such as Lovaza® and Omtryg® or a bioequivalent version of any of these.

In a further aspect, there is provided a combination of dapagliflozin with an icosapent ethyl product, such as Vascepa®.

In another aspect of the invention there is provided a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof.

The two components of the combination of the invention may be administered sequentially or at different times of the day, according to the standard dosing schedule for each component. In one aspect, they are dosed together, for example all in the morning.

Each component of the combination is conveniently administered in an oral dosage form. For example, conveniently, dapagliflozin is conveniently administered as a tablet, in dosages of 2.5 mg, 5 mg or 10 mg of dapagliflozin, and an OM3-CA composition is conveniently administered as a capsule, preferably a coated capsule as hereinbefore described. In certain embodiments, at least about 2 g of the OM3-CA composition is administered per day. In some embodiments, at least about 3 g of the OM3-CA composition is administered per day. In certain embodiments, at least about 4 g of the OM3-CA composition is administered per day. In certain embodiments, at least about 1 g of the OM3-CA composition is administered per day. Typically, the OM3-CA is administered as a plurality of unit dosage forms, such as those described above. Thus, in certain embodiments, at least 2 unit dosage forms, each comprising 1 g of the OM3-CA composition, are administered per day. In various embodiments, at least 3 unit dosage forms, each comprising 1 g of an OM3-CA, are administered per day. In particular embodiments, at least 4 unit dosage forms, each comprising 1 g of the OM3-CA, are administered per day. In one aspect, in the above embodiments, the OM3-CA composition is provided as Epanova®.

In one aspect, a combination of 2.5 mg, 5 mg or 10 mg of dapagliflozin and 1 g, 2 g or 4 g of an OM3-CA is provided.

In one aspect, a combination of 2.5 mg, 5 mg or 10 mg of dapagliflozin and 1 g, 2 g or 4 g of Epanova® or a bio-equivalent version thereof is provided.

In one aspect, a combination of 2.5 mg, 5 mg or 10 mg of dapagliflozin and 1 g, 2 g or 4 g of Epanova® is provided.

In another aspect, a combination of 5 mg or 10 mg of dapagliflozin and 2 g or 4 g of Epanova® is provided.

In another aspect, a combination of 10 mg dapagliflozin and 4 g of Epanova® is provided. Suitably, 10 mg dapagliflozin is administered as a single tablet, and 4 g of Epanova® is administered as four 1 g capsules. Conveniently, this total of five dosage forms may be administered together (although swallowed individually), for example all in the morning.

Suitable omega-3 ethyl ester containing composition dosages are set out in the commercial package inserts, prescribing information and/or labels for Lovaza®, Vascepa® and Omtryg®, or generic marketed versions thereof.

For example, Lovaza®, Vascepa® and Omtryg® may each be used as a 4 g per day dose.

In one aspect, a combination of 2.5 mg, 5 mg or 10 mg of dapagliflozin and up to 4 g of Lovaza® or a bio-equivalent version thereof is provided. In another aspect, a combination of 4 g of Lovaza® or a bio-equivalent version thereof and 10 mg dapagliflozin is provided.

In another aspect, a plurality of unit dosage forms as above-described may usefully be packaged together in a dosage kit to increase ease of use and patient compliance.

In certain embodiments, the dosage kit is a bottle. In other embodiments, the plurality of dosage forms is packaged in blister packs, a plurality of which blister packs may optionally be packaged together in a box or other enclosure. Typically, whether in a bottle or one or more blister packs, the plurality of unit dosage forms is sufficient for 30 days, 60 days, or 90 days of dosing. Thus, in selected embodiments, in which the unit dosage form is a capsule that encapsulates approximately one gram of the pharmaceutical composition as described herein above, the dosage kit comprises 30, 60, 90, 120, 150, 180, 240, 270, 300, 330 or 360 such capsules. The dosage kit also comprises 30, 60 or 90 tablets of dapagliflozin.

In various embodiments, the plurality of unit dosage forms is packaged under an inert gas, such as nitrogen or a noble gas, or is packaged under vacuum.

In another aspect, the combination of the invention may be presented as a fixed-dose combination, ie in a single dosage form.

In another aspect, there is provided a combination of an SGLT-2 inhibitor and an OM3-CA product, such as Epanova® or a bioequivalent version thereof, for use as a medicament.

In a further aspect, there is provided a combination of an SGLT-2 inhibitor selected from dapagliflozin, canagliflozin, remogliflozin etabonate, ipragliflozin and empagliflozin with an OM3-CA product, such as Epanova® or a bio-equivalent version thereof, for use as a medicament.

In a further aspect, there is provided a combination of dapagliflozin with an OM3-CA product, such as Epanova® or a bioequivalent version thereof, for use as a medicament.

In a further aspect, there is provided a combination of an SGLT-2 inhibitor with an OM3-EE product, such as Lovaza® or Omtryg® or a bioequivalent version of any of these, for use as a medicament.

In a further aspect, there is provided a combination of an SGLT-2 inhibitor with an icosapent ethyl product, such as Vascepa® or a bioequivalent version thereof, for use as a medicament.

In a further aspect, there is provided a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these, for use as a medicament.

In a further aspect, there is provided a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, for use as a medicament.

In a further aspect, there is provided a combination of dapagliflozin with an OM3-EE product, such as Lovaza® or Omtryg® or a bioequivalent version of any of these, for use as a medicament.

In a further aspect, there is provided a combination of dapagliflozin with an icosapent ethyl product, such as Vascepa® or a bioequivalent version thereof, for use as a medicament.

In another aspect of the invention there is provided a combination of dapagliflozin and an OM3-CA product for use as a medicament.

In another aspect of the invention there is provided a combination of an SGLT-2 inhibitor or a pharmaceutically acceptable salt thereof, a stereoisomer thereof, or a prodrug ester thereof and an omega-3 fatty acid composition (wherein the omega-3 fatty acid composition comprises one or more omega-3 fatty acids which may be present as acids, esters, triglycerides, phospholipids or salts) for use as a medicament for the treatment of NAFLD and/or NASH.

In another aspect of the invention there is provided a combination of an SGLT-2 inhibitor and an OM3-CA composition for use as a medicament for the treatment of NAFLD and/or NASH.

In another aspect, there is provided a combination of an SGLT-2 inhibitor and an OM3-CA product, such as Epanova® or a bioequivalent version thereof, for use as a medicament for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an OM3-CA product, such as Epanova® or a bio-equivalent version thereof, for use as a medicament for the treatment of NAFLD and/or NASH.

In a further aspect, there is provided a combination of dapagliflozin with an OM3-CA product, such as Epanova® or a bioequivalent version thereof, for use as a medicament for the treatment of NAFLD and/or NASH.

In a further aspect, there is provided a combination of an SGLT-2 inhibitor with an OM3-EE product, such as Lovaza® or Omtryg® or a bioequivalent version of any of these, for use as a medicament for the treatment of NAFLD and/or NASH.

In another aspect of the invention there is provided a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof, for use as a medicament. In one embodiment of this aspect, the SGLT-2 inhibitor is selected from dapagliflozin, canagliflozin, remogliflozin etabonate, ipragliflozin and empagliflozin; for example dapagliflozin.

In a further aspect, there is provided a combination of an SGLT-2 inhibitor with an icosapent ethyl product, such as Vascepa® or a bioequivalent version thereof, for use as a medicament for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these, for use as a medicament for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, for use as a medicament for the treatment of NAFLD and/or NASH.

In a further aspect, there is provided a combination of dapagliflozin with an OM3-EE product, such as Lovaza® or Omtryg® or a bioequivalent version of any of these, for use as a medicament for the treatment of NAFLD and/or NASH.

In another aspect, there is provided a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof, for use as a medicament for the treatment of NAFLD and/or NASH. In one embodiment of this aspect, the SGLT-2 inhibitor is selected from dapagliflozin, canagliflozin, remogliflozin etabonate, ipragliflozin and empagliflozin; for example dapagliflozin.

In a further aspect, there is provided a combination of dapagliflozin with an icosapent ethyl product, such as Vascepa® or a bioequivalent version thereof, for use as a medicament for the treatment of NAFLD and/or NASH.

In another aspect of the invention there is provided a combination of dapagliflozin and an OM3-CA composition for use as a medicament for the treatment of NAFLD and/or NASH.

In another aspect, there is provided a combination of dapagliflozin and Epanova® for use as a medicament for the treatment of NAFLD and/or NASH.

In another aspect, there is provided a combination of an SGLT-2 inhibitor or a pharmaceutically acceptable salt thereof, a stereoisomer thereof, or a prodrug ester thereof and an omega-3 fatty acid composition (wherein the omega-3 fatty acid composition comprises one or more omega-3 fatty acids which may be present as acids, esters, triglycerides, phospholipids or salts) for use as a medicament for reducing fat accumulation in the liver of a human for the treatment of NAFLD and/or NASH.

In another aspect, there is provided a combination of an SGLT-2 inhibitor and an OM3-CA composition for use as a medicament for reducing fat accumulation in the liver of a human for the treatment of NAFLD and/or NASH.

In another aspect, there is provided a combination of an SGLT-2 inhibitor and an OM3-CA product, such as Epanova® or a bioequivalent version thereof, for use as a medicament for reducing fat accumulation in the liver of a human for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an OM3-CA product, such as Epanova® or a bio-equivalent version thereof, for use as a medicament for reducing fat accumulation in the liver of a human for the treatment of NAFLD and/or NASH.

In a further aspect, there is provided a combination of dapagliflozin with an OM3-CA product, such as Epanova® or a bioequivalent version thereof, for use as a medicament for reducing fat accumulation in the liver of a human for the treatment of NAFLD and/or NASH.

In a further aspect, there is provided a combination of an SGLT-2 inhibitor with an OM3-EE product, such as Lovaza® or Omtryg® or a bioequivalent version of any of these, for use as a medicament for reducing fat accumulation in the liver of a human for the treatment of NAFLD and/or NASH.

In a further aspect, there is provided a combination of an SGLT-2 inhibitor with an icosapent ethyl product, such as Vascepa® or a bioequivalent version thereof, for use as a medicament for reducing fat accumulation in the liver of a human for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these, for use as a medicament for reducing fat accumulation in the liver of a human for the treatment of NAFLD and/or NASH.

In a further aspect, there is provided a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, for use as a medicament for reducing fat accumulation in the liver of a human for the treatment of NAFLD and/or NASH.

In a further aspect, there is provided a combination of dapagliflozin with an OM3-EE product, such as Lovaza® or Omtryg® or a bioequivalent version of any of these, for use as a medicament for reducing fat accumulation in the liver of a human for the treatment of NAFLD and/or NASH.

In another aspect, there is provided a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, Lovaza® or Epanova®, or bio-equivalent versions thereof, for use as a medicament for reducing fat accumulation in the liver of a human for the treatment of NAFLD and/or NASH. In one embodiment of this aspect, the SGLT-2 inhibitor is selected from dapagliflozin, canagliflozin, remogliflozin etabonate, ipragliflozin and empagliflozin; for example dapagliflozin.

In a further aspect, there is provided a combination of dapagliflozin with an icosapent ethyl product, such as Vascepa® or a bioequivalent version thereof, for use as a medicament for reducing fat accumulation in the liver of a human for the treatment of NAFLD and/or NASH.

In another aspect of the invention there is provided a combination of dapagliflozin and an OM3-CA composition for use as a medicament for reducing fat accumulation in the liver of a human for the treatment of NAFLD and/or NASH.

In another aspect of the invention there is provided a combination of dapagliflozin and Epanova® for use as a medicament for reducing fat accumulation in the liver of a human for the treatment of NAFLD and/or NASH.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH, wherein the subject is non-diabetic or diabetic.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH on the basis of their NAFLD Activity Score, optionally in combination with a fibrosis stage score.

In a further aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH on the basis of NAFLD Activity Score, optionally in combination with a fibrosis stage score.

In a further aspect, there is provided a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH on the basis of NAFLD Activity Score, optionally in combination with a fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a combination of an effective dose of Epanova® or a bioequivalent version thereof and an effective dose of dapagliflozin, for use as a medicament for the treatment of NASH in a subject having, or suspected of having NASH on the basis of NAFLD Activity Score, optionally in combination with a fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH on the basis of the subject's steatosis score, lobular inflammation score and ballooning score, optionally in combination with the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH in a subject having, or suspected of having NASH, wherein the subject has normal or substantially normal biliary tract function. In one aspect a normal or substantially normal biliary tract function is determined on the basis of the subject's alkaline phosphatase (ALP) and bilirubin levels.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH; administering the combination; and thereby improving the steatosis, ballooning and/or lobular inflammation condition of said subject, with no worsening of the subject's fibrosis stage score.

In a further aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH; administering the combination; and thereby improving the steatosis, ballooning and/or lobular inflammation condition of said subject, with no worsening of the subject's fibrosis stage score.

In a further aspect, there is provided a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH; administering the combination; and thereby improving the steatosis, ballooning and/or lobular inflammation condition of said subject, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a combination of an effective dose of Epanova® or a bio-equivalent version thereof and an effective dose of dapagliflozin, for use as a medicament for the treatment of NASH wherein the treatment comprises:
selecting a subject having, or suspected of having NASH; administering the combination; and thereby improving the steatosis, ballooning and/or lobular inflammation condition of said subject, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH on the basis of their NAFLD Activity Score; administering the combination; and thereby improving the NAFLD Activity Score of said subject by at least 1 point, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH on the basis of their NAFLD Activity Score; administering the combination; and thereby improving the NAFLD Activity Score of said subject by at least 2 points, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having, or suspected of having NASH on the basis of their NAFLD Activity Score; administering the combination; and thereby improving the steatosis score of said subject by at least 1 point, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5; administering the combination; and thereby improving the NAFLD Activity Score of said subject by at least 1 point, with no worsening of the subject's fibrosis stage score.

In a further aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5; administering the combination; and thereby improving the NAFLD Activity Score of said subject by at least 1 point, with no worsening of the subject's fibrosis stage score.

In a further aspect, there is provided a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5; administering the combination; and thereby improving the NAFLD Activity Score of said subject by at least 1 point, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a combination of an effective dose of Epanova® or a bioequivalent version thereof and an effective dose of dapagliflozin, for use as a medicament for the treatment of NASH, wherein the treatment comprises:
selecting a subject, previously diagnosed with Type II diabetes mellitus, having a NAFLD Activity Score score greater than or equal to 5;
administering the combination; and thereby improving the NAFLD Activity Score of said subject by at least 1 point, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5;
administering the combination; and thereby improving the NAFLD Activity Score of said subject by at least 2 points, with no worsening of the subject's fibrosis stage score.

In a further aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5;
administering the combination; and thereby improving the NAFLD Activity Score of said subject by at least 2 points, with no worsening of the subject's fibrosis stage score.

In a further aspect, there is provided a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score score greater than or equal to 5;
administering the combination; and thereby improving the NAFLD Activity Score of said subject by at least 2 points, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a combination of an effective dose of Epanova® or a bioequivalent version thereof and an effective dose of dapagliflozin, for use as a medicament for the treatment of NASH, wherein the treatment comprises:
selecting a subject, previously diagnosed with Type II diabetes mellitus, having a NAFLD Activity Score greater than or equal to 5;
administering the combination; and thereby improving the NAFLD Activity Score of said subject by at least 2 points, with no worsening of the subject's fibrosis stage score.

In a further aspect, there is provided a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score greater than or equal to 5;
administering the combination; and thereby improving the steatosis score of said subject by at least 1 point, with no worsening of the subject's fibrosis stage score.

In a further aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score greater than or equal to 5;
administering the combination; and thereby improving the steatosis score of said subject by at least 1 point, with no worsening of the subject's fibrosis stage score.

In a further aspect, there is provided a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score greater than or equal to 5;
administering the combination; and thereby improving the improving the steatosis score of the subject by at least 1 point, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a combination of an effective dose of Epanova® or a bioequivalent version thereof and an effective dose of dapagliflozin, for use as a medicament for the treatment of NASH, wherein the treatment comprises:
selecting a subject, previously diagnosed with Type II diabetes mellitus, having a NAFLD Activity Score greater than or equal to 5;
administering the combination; and thereby improving the steatosis score of the subject by at least 1 point, with no worsening of the subject's fibrosis stage score.

In a further aspect, there is provided a combination of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, for use as a medicament for the treatment of NASH wherein the treatment comprises:
selecting a subject having a NAFLD Activity Score greater than or equal to 5;
determining the subject's ALP and bilirubin serum levels; administering the combination; and thereby improving the steatosis condition of said subject, with no worsening of the subject's fibrosis stage score.

In some aspects, selecting a subject having or suspected of having NAFLD and/or NASH comprises selecting a subject having a NAFLD Activity Score greater than or equal to 5; or steatosis score equal or greater than 1; or lobular inflammation score equal to or greater than 1; or ballooning score equal to or greater than 1; or fibrosis score equal to or greater than 1.

In a particular aspect, treatment with the omega-3 fatty acid composition and the SGLT-2 inhibitor is particularly effective at improving the subject's steatosis score, and so particularly effective at reducing liver fat.

Therefore in one aspect, there is provided a combination of an effective dose of an OM3-CA composition and an effective dose of an SGLT-2 inhibitor or a pharmaceutically acceptable salt thereof, a stereoisomer thereof, or a prodrug ester thereof, for use as a medicament for the reduction of liver fat in a subject, wherein the use comprises selecting a subject who has been diagnosed with Type II diabetes mellitus and diagnosed as having raised liver fat (>5.5% as assessed by MRI or MRS), administering the combination; and thereby reducing the liver fat content by at least 15%, such as at least 20%, such as at least 25% (as assessed by MRI or MRS).

In one aspect, there is provided a combination of an effective dose of an Epanova® or a bioequivalent version thereof and an effective dose of dapagliflozin, for use as a medicament for the reduction of liver fat in a subject, wherein the use comprises selecting a subject who has been diagnosed with Type II diabetes mellitus and diagnosed as having raised liver fat (>5.5% as assessed by MRI or MRS), administering the combination; and thereby reducing the liver fat content by at least 15%, such as at least 20%, such as at least 25% (as assessed by MRI or MRS).

In one aspect, there is provided a combination of an effective dose of Epanova® or a bioequivalent version thereof and an effective dose of dapagliflozin, for use as a medicament for reduction of liver fat in a subject who has been diagnosed with Type II diabetes mellitus and diagnosed as having raised liver fat (>5.5% as assessed by MRI or MRS).

In one aspect, there is provided a combination of an effective dose of Epanova® or a bioequivalent version thereof and an effective dose of dapagliflozin, for use as a medicament for reduction of liver fat and for reduction in plasma triglyceride level, in a subject who has been diagnosed with Type II diabetes mellitus and diagnosed as having raised liver fat (>5.5% as assessed by MRI or MRS).

In one aspect, there is provided a combination of an effective dose of Epanova® or a bioequivalent version thereof and an effective dose of dapagliflozin, for use as a medicament for reduction of liver fat and for raising of plasma EPA and/or DHA levels, in a subject who has been diagnosed with Type II diabetes mellitus and diagnosed as having raised liver fat (>5.5% as assessed by MRI or MRS).

In another aspect, there is provided a combination of an effective dose of Epanova® or a bioequivalent version thereof and an effective dose of dapagliflozin, for use as a medicament for the reduction of liver fat and for the reduction of cell death and/or ballooning, in a subject who has been diagnosed with Type II diabetes mellitus and diagnosed as having raised liver fat (>5.5% as assessed by MRI or MRS).

In another aspect, there is provided a combination of an effective dose of Epanova® or a bioequivalent version thereof and an effective dose of dapagliflozin for use in the reduction of liver fat and the reduction of liver inflammation, in a subject in need thereof.

In one aspect, there is provided a combination of an effective dose of Epanova® or a bioequivalent version thereof and an effective dose of dapagliflozin for use in the reduction of liver fat in a subject who is overweight (with a BMI of >25), has been diagnosed as having raised liver fat (>5.5% as assessed by MRI or MRS) and optionally has also been diagnosed with Type II diabetes mellitus.

In one aspect, there is provided a combination of an effective dose of Epanova® or a bioequivalent version thereof and an effective dose of dapagliflozin for use in the reduction of liver fat and reduction in plasma triglyceride level, in a subject who is overweight (with a BMI of >25), who has been diagnosed as having raised liver fat (>5.5% as assessed by MRI or MRS), and optionally has also been diagnosed with Type II diabetes mellitus.

In one aspect, there is provided a combination of an effective dose of Epanova® or a bioequivalent version thereof and an effective dose of dapagliflozin for use in the reduction of liver fat and increase of plasma EPA and/or DHA levels, in a subject who is overweight (with a BMI of >25), who has been diagnosed as having raised liver fat (>5.5% as assessed by MRI or MRS), and optionally has also been diagnosed with Type II diabetes mellitus.

In another aspect, there is provided a combination of an effective dose of Epanova® or a bioequivalent version thereof and an effective dose of dapagliflozin for use in the reduction of liver fat and the reduction of hepatic cell death and/or ballooning, in a subject who is overweight (with a BMI of >25), who has been diagnosed as having raised liver fat (>5.5% as assessed by MRI or MRS), and optionally has also been diagnosed with Type II diabetes mellitus.

In another aspect, there is provided a combination of an effective dose of Epanova® or a bioequivalent version thereof and an effective dose of dapagliflozin for use in halting progression of liver fibrosis, in a subject in need thereof.

In another aspect, there is provided a combination of an effective dose of Epanova® or a bioequivalent version thereof and an effective dose of dapagliflozin, in a subject who has been diagnosed with NAFLD or NASH, for use in halting progression of NAFLD and/or NASH comprising administering the combination and thereby causing a halt in progression of fibrosis of the subject's liver.

In another aspect there is provided a combination of an effective dose of Epanova® or a bioequivalent version thereof and an effective dose of dapagliflozin for use in the treatment of NASH, in a subject having, or suspected of having NASH, comprising administering the combination and thereby causing a reduction in body weight of the subject.

In another aspect there is provided a combination of an effective dose of Epanova® or a bioequivalent version thereof and an effective dose of dapagliflozin for use in the treatment of NASH, in a subject having, or suspected of having NASH, comprising administering the combination and thereby causing an increase in insulin sensitisation of the subject.

In another aspect there is provided a combination of an effective dose of Epanova® or a bioequivalent version thereof and an effective dose of dapagliflozin for use in the reversal or resolution of NASH, in a subject having NASH, wherein the NASH status of the subject is diagnosed by histopathological assessment.

In one aspect, there is provided a method for treating NAFLD and/or NASH comprising administering an effective dose of an SGLT-2 inhibitor or a pharmaceutically acceptable salt thereof, a stereoisomer thereof, or a prodrug ester thereof and an effective dose of an omega-3 fatty acid composition (wherein omega-3 fatty acids may be present as acids, esters, triglycerides, phospholipids or salts) to a warm-blooded animal in need of such treatment.

In another aspect, there is provided a method for treating NAFLD and/or NASH comprising administering an effective dose of an SGLT-2 inhibitor or a pharmaceutically acceptable salt thereof, a stereoisomer thereof, or a prodrug ester thereof and an effective dose of an OM3-CA composition to a warm-blooded animal in need of such treatment.

In another aspect, there is provided a method for treating NAFLD and/or NASH comprising administering an effective dose of an SGLT-2 inhibitor and an effective dose of an OM3-CA product, such as Epanova® or a bioequivalent version thereof, to a warm-blooded animal in need of such treatment.

In another aspect, there is provided a method for treating NAFLD and/or NASH comprising administering an effective dose of an SGLT-2 inhibitor selected from dapagliflozin, canagliflozin, remogliflozin etabonate, ipragliflozin and empagliflozin, and an effective dose of an OM3-CA product, such as Epanova® or a bioequivalent version thereof, to a warm-blooded animal in need of such treatment.

In another aspect, there is provided a method for treating NAFLD and/or NASH comprising administering an effective dose of dapagliflozin and an effective dose of an OM3-CA product, such as Epanova® or a bioequivalent version thereof, to a warm-blooded animal in need of such treatment.

In another aspect, there is provided a method for treating NAFLD and/or NASH comprising administering an effective dose of an SGLT-2 inhibitor and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising administering an effective dose of an SGLT-2 inhibitor or a pharmaceutically acceptable salt thereof, a stereoisomer thereof, or a prodrug ester thereof and an effective dose of an omega-3 fatty acid composition wherein the omega-3 fatty acid composition comprises DHA (in free acid, ester, triglyceride or phospholipid form) and is, for example, Lovaza® or Epanova®, or bio-equivalent versions thereof, to a warm-blooded animal in need of such treatment. In one embodiment of this aspect, the SGLT-2 inhibitor is selected from dapagliflozin, canagliflozin, remogliflozin etabonate, ipragliflozin and empagliflozin; for example dapagliflozin.

In another aspect, there is provided a method for treating NAFLD and/or NASH comprising administering an effective dose of an SGLT-2 inhibitor and an effective dose of an icosapent ethyl product, such as Vascepa® or a bioequivalent version thereof, to a warm-blooded animal in need of such treatment.

In another aspect, there is provided a method for treating NAFLD and/or NASH comprising administering an effective dose of an SGLT-2 inhibitor selected from dapagliflozin, canagliflozin, remogliflozin etabonate, ipragliflozin and empagliflozin, and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising administering an effective dose of an SGLT-2 inhibitor selected from dapagliflozin, canagliflozin, remogliflozin etabonate, ipragliflozin and empagliflozin, and an effective dose of an icosapent ethyl product, such as Vascepa® or a bioequivalent version thereof, to a warm-blooded animal in need of such treatment.

In another aspect, there is provided a method for treating NAFLD and/or NASH comprising administering an effective dose of dapagliflozin and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising administering an effective dose of dapagliflozin and an effective dose of an icosapent ethyl product, such as Vascepa® or a bioequivalent version thereof, to a warm-blooded animal in need of such treatment.

In one aspect, there is provided a method for treating NAFLD and/or NASH comprising administering an effective dose of dapagliflozin and an effective dose of an OM3-CA composition to a warm-blooded animal in need of such treatment.

In one aspect, there is provided a method for treating NAFLD and/or NASH comprising administering an effective dose of dapagliflozin and an effective dose of Epanova® to a warm-blooded animal in need of such treatment.

In one aspect, there is provided a method for treating NAFLD and/or NASH comprising reducing fat accumulation in the liver of a warm-blooded animal by administering an effective dose of an SGLT-2 inhibitor or a pharmaceutically acceptable salt thereof, a stereoisomer thereof, or a prodrug ester thereof and an effective dose of an omega-3 fatty acid composition (wherein omega-3 fatty acids may be present as acids, esters, triglycerides, phospholipids or salts) to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor or a pharmaceutically acceptable salt thereof, a stereoisomer thereof, or a prodrug ester thereof and an effective dose of an OM3-CA composition to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor and an effective dose of an OM3-CA product, such as Epanova® or a bioequivalent version thereof, to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor selected from dapagliflozin, canagliflozin, remogliflozin etabonate, ipragliflozin and empagliflozin, and an effective dose of an OM3-CA product, such as Epanova® or a bioequivalent version thereof, to a warm-blooded animal in need of such treatment.

In another aspect, there is provided a method for treating NAFLD and/or NASH comprising reducing fat accumulation in the liver of a warm-blooded animal by administering an effective dose of dapagliflozin and an effective dose of an OM3-CA product, such as Epanova® or a bioequivalent version thereof, to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor or a pharmaceutically acceptable salt thereof, a stereoisomer thereof, or a prodrug ester thereof and an effective dose of an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof, to a warm-blooded animal in need of such treatment. In one embodiment of this aspect, the SGLT-2 inhibitor is selected from dapagliflozin, canagliflozin, remogliflozin etabonate, ipragliflozin and empagliflozin; for example dapagliflozin.

In another aspect, there is provided a method for treating NAFLD and/or NASH comprising reducing fat accumulation in the liver of a warm-blooded animal by administering an effective dose of an SGLT-2 inhibitor and an effective dose of an icosapent ethyl product, such as Vascepa® or a bioequivalent version thereof, to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor selected from dapagliflozin, canagliflozin, remogliflozin etabonate, ipragliflozin and empagliflozin, and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising reducing fat accumulation in the liver of a warm-blooded animal by administering an effective dose of an SGLT-2 inhibitor selected from dapagliflozin, canagliflozin, remogliflozin etabonate, ipragliflozin and empagliflozin, and an effective dose of an icosapent ethyl product, such as Vascepa® or a bioequivalent version thereof, to a warm-blooded animal in need of such treatment.

In another aspect, there is provided a method for treating NAFLD and/or NASH comprising reducing fat accumulation in the liver of a warm-blooded animal by administering an effective dose of dapagliflozin and an effective dose of an OM3-EE product, such as Lovaza® or Omtryg® or a bioequivalent version of any of these, to a warm-blooded animal in need of such treatment.

In another aspect, there is provided a method for treating NAFLD and/or NASH comprising reducing fat accumulation in the liver of a warm-blooded animal by administering an effective dose of dapagliflozin and an effective dose of an icosapent ethyl product, such as Vascepa® or a bioequivalent version thereof, to a warm-blooded animal in need of such treatment.

In one aspect, there is provided a method for treating NAFLD and/or NASH comprising reducing fat accumulation in the liver of a warm-blooded animal by administering an effective dose of dapagliflozin and an effective dose of an OM3-CA product to a warm-blooded animal in need of such treatment.

In one aspect, there is provided a method for treating NAFLD and/or NASH comprising reducing fat accumulation in the liver of a warm-blooded animal by administering an effective dose of dapagliflozin and an effective dose of Epanova® to a warm-blooded animal in need of such treatment.

In a further aspect, there is provided a method for treating NASH, in a subject in need thereof, comprising selecting a subject having, or suspected of having NASH, wherein the subject is non diabetic or diabetic, and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts).

In a further aspect, there is provided a method for treating NASH, in a subject in need thereof, comprising selecting a subject having, or suspected of having NASH on the basis of clinical and histopathological diagnosis, and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts).

In a further aspect, there is provided a method for treating NASH, in a subject in need thereof, comprising selecting a subject having, or suspected of having NASH on the basis of NAFLD Activity Score, optionally in combination with a fibrosis stage score, and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts).

In a further aspect, there is provided a method for treating NASH, in a subject in need thereof, comprising selecting a subject having, or suspected of having NASH on the basis of NAFLD Activity Score, optionally in combination with a fibrosis stage score, and administering an effective dose of an SGLT-2 inhibitor or a pharmaceutically acceptable salt thereof, a stereoisomer thereof, or a prodrug ester thereof, and an effective dose of an OM3-CA composition.

In a further aspect, there is provided a method for treating NASH, in a subject in need thereof, comprising selecting a subject having, or suspected of having NASH on the basis of NAFLD Activity Score, optionally in combination with a fibrosis stage score, and administering an effective dose of an SGLT-2 inhibitor or a pharmaceutically acceptable salt thereof, a stereoisomer thereof, or a prodrug ester thereof, and an effective dose of an OM3-CA product, such as Epanova® or a bioequivalent version thereof. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a method for treating NASH, in a subject in need thereof, comprising selecting a subject, previously diagnosed with Type II diabetes mellitus, having, or suspected of having NASH on the basis of NAFLD Activity Score, optionally in combination with a fibrosis stage score, and administering dapagliflozin and Epanova® or a bioequivalent version thereof.

In a further aspect, there is provided a method for treating NASH, in a subject in need thereof, comprising selecting a subject having, or suspected of having NASH on the basis of the subject's steatosis score, lobular inflammation score and ballooning score, optionally in combination with the subject's fibrosis stage score, and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts).

In a further aspect, there is provided a method for treating NASH, in a subject in need thereof, comprising selecting a subject having, or suspected of having NASH, wherein the subject has normal or substantially normal biliary tract function, and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts). In one aspect a normal or substantially normal biliary tract function is determined on the basis of the subject's alkaline phosphatase (ALP) and bilirubin levels.

In a further aspect, there is provided a method for treating NASH, in a subject in need thereof, comprising:
selecting a subject having, or suspected of having NASH; administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the steatosis, ballooning and/or lobular inflammation condition of said subject, with no worsening of the subject's fibrosis stage score.

In a further aspect, there is provided a method for treating NASH, in a subject in need thereof, comprising:
selecting a subject having, or suspected of having NASH; administering an effective dose of an SGLT-2 inhibitor or a pharmaceutically acceptable salt thereof, a stereoisomer thereof, or a prodrug ester thereof, and an effective dose of an OM3-CA; and thereby improving the steatosis, ballooning and/or lobular inflammation condition of said subject, with no worsening of the subject's fibrosis stage score.

In a further aspect, there is provided a method for treating NASH, in a subject in need thereof, comprising:
selecting a subject having, or suspected of having NASH; administering an effective dose of an SGLT-2 inhibitor or a pharmaceutically acceptable salt thereof, a stereoisomer thereof, or a prodrug ester thereof, and an effective dose of an OM3-CA product, such as Epanova® or a bioequivalent version thereof. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a method for treating NASH, in a subject in need thereof, comprising:
selecting a subject having, or suspected of having NASH; administering an effective dose of dapagliflozin, and an effective dose of Epanova® or a bio-equivalent version thereof; and thereby improving the steatosis, ballooning and/or lobular inflammation condition of said subject, with no worsening of the subject's fibrosis stage score.

In a further aspect, there is provided a method for treating NASH, in a subject in need thereof, comprising:
selecting a subject having, or suspected of having NASH on the basis of their NAFLD Activity Score;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the NAFLD Activity Score of said subject by at least 1 point, with no worsening of the subject's fibrosis stage score.

In a further aspect, there is provided a method for treating NASH, in a subject in need thereof, comprising:
selecting a subject having, or suspected of having NASH on the basis of their NAFLD Activity Score;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the NAFLD Activity Score of said subject by at least 2 points, with no worsening of the subject's fibrosis stage score.

In a further aspect, there is provided a method for treating NASH, in a subject in need thereof, comprising:
selecting a subject having, or suspected of having NASH on the basis of their NAFLD Activity Score;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the steatosis score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the NAFLD Activity Score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;

administering an effective dose of an SGLT-2 inhibitor or a pharmaceutically acceptable salt thereof, a stereoisomer thereof, or a prodrug ester thereof, and an effective dose of an OM3-CA composition; and thereby improving the NAFLD Activity Score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an OM3-CA product, such as Epanova® or a bioequivalent version thereof; and thereby improving the NAFLD Activity Score of said subject by at least 1 point, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a method for treating NASH, in a subject in need thereof, comprising:
selecting a subject, previously diagnosed with Type II diabetes mellitus, having a NAFLD Activity Score greater than or equal to 5;
administering an effective dose of dapagliflozin, and an effective dose of Epanova® or a bioequivalent version thereof;
and thereby improving the NAFLD Activity Score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the NAFLD Activity Score of said subject by at least 2 points, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an OM3-CA composition; and thereby improving the NAFLD Activity Score of said subject by at least 2 points, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an OM3-CA product, such as Epanova® or a bioequivalent version thereof; and thereby improving the NAFLD Activity Score of said subject by at least 2 points, with no worsening of the subject's fibrosis stage score. Suitably in this aspect, the SGLT-2 inhibitor is selected from dapagliflozin, canagliflozin, remogliflozin etabonate, ipragliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a method for treating NASH, in a subject in need thereof, comprising:
selecting a subject, previously diagnosed with Type II diabetes mellitus, having a NAFLD Activity Score greater than or equal to 5;
administering an effective dose of dapagliflozin, and an effective dose of Epanova® or a bioequivalent version thereof;
and thereby improving the NAFLD Activity Score of said subject by at least 2 points, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the steatosis score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an OM3-CA composition; and thereby improving the steatosis score of said subject by at least 1 point, with no worsening of the subject's fibrosis stage score.

In a further aspect, there is provided a method for treating NASH, in a subject in need thereof, comprising:
selecting a subject having a NAFLD Activity Score greater than or equal to 5;
administering an effective dose of an SGLT-2 inhibitor or a pharmaceutically acceptable salt thereof, a stereoisomer thereof, or a prodrug ester thereof, and an effective dose of an OM3-CA product, such as Epanova® or a bioequivalent version thereof; and thereby improving the steatosis score of said subject by at least 1 point, with no worsening of the subject's fibrosis stage score. Suitably in this aspect, the SGLT-2 inhibitor is selected from dapagliflozin, canagliflozin, remogliflozin etabonate, ipragliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided a method for treating NASH, in a subject in need thereof, comprising:
selecting a subject, previously diagnosed with Type II diabetes mellitus, having a NAFLD Activity Score greater than or equal to 5;
administering an effective dose of dapagliflozin, and an effective dose of Epanova® or a bioequivalent version thereof;

and thereby improving the steatosis score of said subject by at least 1 point, with no worsening of the subject's fibrosis stage score.

In a further aspect, there is provided a method for treating NASH, in a subject in need thereof, comprising: selecting a subject having a NAFLD Activity Score greater than or equal to 5; determining the subject's ALP and bilirubin serum levels; and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the steatosis condition of said subject, with no worsening of the subject's fibrosis stage score.

In some aspects, selecting a subject having or suspected of having NAFLD and/or NASH comprises selecting a subject having a NAFLD Activity Score greater than or equal to 5; or steatosis score equal or greater than 1; or lobular inflammation score equal to or greater than 1; or ballooning score equal to or greater than 1; or fibrosis score equal to or greater than 1.

In a particular aspect, treatment with the omega-3 fatty acid composition and the SGLT-2 inhibitor is particularly effective at improving the subject's steatosis score, and so particularly effective at reducing liver fat.

Therefore in one aspect, there is provided a method for the reduction of liver fat in a subject comprising selecting a subject who has been diagnosed with Type II diabetes mellitus and diagnosed as having raised liver fat (>5.5% as assessed by MRI or MRS); administering a combination of an effective dose of an OM3-CA composition and an effective dose of an SGLT-2 inhibitor or a pharmaceutically acceptable salt thereof, a stereoisomer thereof, or a prodrug ester thereof; and thereby reducing the liver fat content by at least 15%, such as at least 20%, such as at least 25% (as assessed by MRI or MRS).

In one aspect, there is provided a method for the reduction of liver fat in a subject comprising selecting a subject who has been diagnosed with Type II diabetes mellitus and diagnosed as having raised liver fat (>5.5% as assessed by MRI or MRS); administering a combination of an effective dose of Epanova® or a bioequivalent version thereof and an effective dose of dapagliflozin; and thereby reducing the liver fat content by at least 15%, such as at least 20%, such as at least 25% (as assessed by MRI or MRS).

In one aspect, there is provided a method for the reduction of liver fat in a subject who has been diagnosed with Type II diabetes mellitus and diagnosed as having raised liver fat (>5.5% as assessed by MRI or MRS), comprising administering a combination of an effective dose of Epanova® or a bioequivalent version thereof and an effective dose of dapagliflozin.

In one aspect, there is provided a method for the reduction of liver fat and reduction in plasma triglyceride level, in a subject who has been diagnosed with Type II diabetes mellitus and diagnosed as having raised liver fat (>5.5% as assessed by MRI or MRS) comprising administering a combination of an effective dose of Epanova® or a bioequivalent version thereof and an effective dose of dapagliflozin.

In one aspect, there is provided a method for the reduction of liver fat and increase of plasma EPA and/or DHA levels, in a subject who has been diagnosed with Type II diabetes mellitus and diagnosed as having raised liver fat (>5.5% as assessed by MRI or MRS) comprising administering a combination of an effective dose of Epanova® or a bioequivalent version thereof and an effective dose of dapagliflozin.

In another aspect, there is provided a method for the reduction of liver fat and the reduction of cell death and/or ballooning, in a subject who has been diagnosed with Type II diabetes mellitus and diagnosed as having raised liver fat (>5.5% as assessed by MRI or MRS) comprising administering a combination of an effective dose of Epanova® or a bioequivalent version thereof and an effective dose of dapagliflozin.

In another aspect, there is provided a method for the reduction of liver fat and the reduction of liver inflammation, in a subject in need thereof, comprising administering a combination of an effective dose of Epanova® or a bioequivalent version thereof and an effective dose of dapagliflozin.

In one aspect, there is provided a method for the reduction of liver fat in a subject who has been diagnosed with Type II diabetes mellitus, is overweight (with a BMI of >25), and who has been diagnosed as having raised liver fat (>5.5% as assessed by MRI or MRS), comprising administering a combination of an effective dose of Epanova® or a bioequivalent version thereof and an effective dose of dapagliflozin.

In one aspect, there is provided a method for the reduction of liver fat and reduction in plasma triglyceride level, in a subject who is overweight (with a BMI of >25), who has been diagnosed as having raised liver fat (>5.5% as assessed by MRI or MRS), and optionally has also been diagnosed with Type II diabetes mellitus, comprising administering a combination of an effective dose of Epanova® or a bioequivalent version thereof and an effective dose of dapagliflozin.

In one aspect, there is provided a method for the reduction of liver fat and increase of plasma EPA and/or DHA levels, in a subject who is overweight (with a BMI of >25), has been diagnosed as having raised liver fat (>5.5% as assessed by MRI or MRS), and optionally has been diagnosed with Type II diabetes mellitus, comprising administering a combination of an effective dose of Epanova® or a bioequivalent version thereof and an effective dose of dapagliflozin.

In another aspect, there is provided a method for the reduction of liver fat and the reduction of hepatic cell death and/or ballooning, in a subject who is overweight (with a BMI of >25), has been diagnosed as having raised liver fat (>5.5% as assessed by MRI or MRS) and optionally has been diagnosed with Type II diabetes mellitus, comprising administering a combination of an effective dose of Epanova® or a bioequivalent version thereof and an effective dose of dapagliflozin.

In another aspect, there is provided a method for halting the progression of liver fibrosis, in a subject in need thereof, comprising administering a combination of an effective dose of Epanova® or a bioequivalent version thereof and an effective dose of dapagliflozin.

In another aspect, there is provided a method for halting progression of NAFLD and/or NASH, in a subject who has been diagnosed with NAFLD or NASH, comprising administering a combination of an effective dose of Epanova® or a bioequivalent version thereof and an effective dose of dapagliflozin and thereby causing a halt in progression of fibrosis of the subject's liver.

In another aspect there is provided a method for treatment of NASH, in a subject having, or suspected of having NASH, comprising administering a combination of an effective dose of Epanova® or a bioequivalent version thereof and an effective dose of dapagliflozin and thereby causing a reduction in body weight of the subject.

In another aspect there is provided a method for treatment of NASH, in a subject having, or suspected of having NASH, comprising administering a combination of an effective dose of Epanova® or a bioequivalent version thereof and an effective dose of dapagliflozin and thereby causing an increase in insulin sensitisation of the subject.

In a further aspect, there is provided a method for treating NASH, in a subject in need thereof, comprising:
selecting a subject having a NAFLD Activity Score greater than or equal to 5; determining the subject's ALP and bilirubin serum levels; and administering an effective dose of an SGLT-2 inhibitor or a pharmaceutically acceptable salt thereof, a stereoisomer thereof, or a prodrug ester thereof, and an effective dose of an omega-3 fatty acid composition (wherein the omega-3 fatty acid composition contains one or more omega-3 fatty acids which may be present as acids, esters, triglycerides, phospholipids or salts); and thereby improving the steatosis and lobular inflammation condition of said subject, with no worsening of the subject's fibrosis stage score.

In some aspects, selecting a subject having or suspected of having NAFLD and/or NASH comprises selecting a subject having a NAFLD Activity Score greater than or equal to 5; or steatosis score equal or greater than 1; or lobular inflammation score equal to or greater than 1; or ballooning score equal to or greater than 1; or fibrosis score equal to or greater than 1.

In another aspect there is provided a method for reversal or resolution of NASH, in a subject having NASH, wherein the NASH status of the subject has been diagnosed by histopathological assessment, comprising administering the combination of an effective dose of Epanova® or a bioequivalent version thereof and an effective dose of dapagliflozin.

In a further aspect, there is provided the use of a combination of an SGLT-2 inhibitor or a pharmaceutically acceptable salt thereof, a stereoisomer thereof, or a prodrug ester thereof, and an omega-3 fatty acid composition (wherein the omega-3 fatty acid composition comprises one or more omega-3 fatty acids which may be present as acids, esters, triglycerides, phospholipids or salts) in the manufacture of a medicament for the treatment of NAFLD and/or NASH.

In a further aspect, there is provided the use of a combination of an SGLT-2 inhibitor and an OM3-CA product, such as Epanova® or a bioequivalent version thereof, in the manufacture of a medicament for the treatment of NAFLD and/or NASH.

In a further aspect, there is provided the use of a combination of an SGLT-2 inhibitor selected from dapagliflozin, canagliflozin, remogliflozin etabonate, ipragliflozin and empagliflozin with an OM3-CA product, such as Epanova® or a bioequivalent version thereof, in the manufacture of a medicament for the treatment of NAFLD and/or NASH.

In a further aspect, there is provided the use of a combination of dapagliflozin with an OM3-CA product, such as Epanova® or a bioequivalent version thereof, in the manufacture of a medicament for the treatment of NAFLD and/or NASH.

In a further aspect, there is provided the use of a combination of an SGLT-2 inhibitor with an OM3-EE product, such as Lovaza® or Omtryg® or a bioequivalent version of any of these, in the manufacture of a medicament for the treatment of NAFLD and/or NASH.

In a further aspect, there is provided the use of a combination of an SGLT-2 inhibitor with an icosapent ethyl product, such as Vascepa® or a bioequivalent version thereof, in the manufacture of a medicament for the treatment of NAFLD and/or NASH.

In a further aspect, there is provided the use of a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these, in the manufacture of a medicament for the treatment of NAFLD and/or NASH.

In another aspect, there is provided the use of a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof, in the manufacture of a medicament for the treatment of NAFLD and/or NASH. In one embodiment of this aspect, the SGLT-2 inhibitor is selected from dapagliflozin, canagliflozin, remogliflozin etabonate, ipragliflozin and empagliflozin; for example dapagliflozin.

In a further aspect, there is provided the use of a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, in the manufacture of a medicament for the treatment of NAFLD and/or NASH.

In a further aspect, there is provided the use of a combination of dapagliflozin with an OM3-EE product, such as Lovaza® or Omtryg® or a bioequivalent version of any of these, in the manufacture of a medicament for the treatment of NAFLD and/or NASH.

In a further aspect, there is provided the use of a combination of dapagliflozin with an icosapent ethyl product, such as Vascepa® or a bioequivalent version thereof, in the manufacture of a medicament for the treatment of NAFLD and/or NASH.

In a further aspect, there is provided the use of a combination of an SGLT-2 inhibitor and an OM3-CA composition in the manufacture of a medicament for the treatment of NAFLD and/or NASH.

In a further aspect, there is provided the use of a combination of an SGLT-2 inhibitor and Epanova® in the manufacture of a medicament for the treatment of NAFLD and/or NASH.

In a further aspect, there is provided the use of a combination of an SGLT-2 inhibitor or a pharmaceutically acceptable salt thereof, a stereoisomer thereof, or a prodrug ester thereof, and an omega-3 fatty acid composition (wherein the omega-3 fatty acid composition comprises one or more omega-3 fatty acids which may be present as acids, esters, triglycerides, phospholipids or salts) in the manufacture of a medicament for reducing fat accumulation in the liver of a human for the treatment of NAFLD and/or NASH.

In a further aspect, there is provided the use of a combination of an SGLT-2 inhibitor and an OM3-CA product, such as Epanova® or a bioequivalent version thereof, in the manufacture of a medicament for reducing fat accumulation in the liver of a human for the treatment of NAFLD and/or NASH.

In a further aspect, there is provided the use of a combination of an SGLT-2 inhibitor selected from dapagliflozin, canagliflozin, remogliflozin etabonate, ipragliflozin and empagliflozin with an OM3-CA product, such as Epanova® or a bioequivalent version thereof, in the manufacture of a medicament for reducing fat accumulation in the liver of a human for the treatment of NAFLD and/or NASH.

In a further aspect, there is provided the use of a combination of dapagliflozin with an OM3-CA product, such as Epanova® or a bioequivalent version thereof, in the manufacture of a medicament for reducing fat accumulation in the liver of a human for the treatment of NAFLD and/or NASH.

In a further aspect, there is provided the use of a combination of an SGLT-2 inhibitor with an OM3-EE product, such as Lovaza® or Omtryg® or a bioequivalent version of any of these, in the manufacture of a medicament for reducing fat accumulation in the liver of a human for the treatment of NAFLD and/or NASH.

In another aspect, there is provided the use of a combination of an SGLT-2 inhibitor or a pharmaceutically acceptable salt thereof, a stereoisomer thereof, or a prodrug ester thereof and an omega-3 fatty acid composition wherein the omega-3 fatty acid composition comprises DHA (in free acid, ester, triglyceride or phospholipid form) and is, for example, provided as Lovaza® or Epanova®, or bio-equivalent versions thereof, in the manufacture of a medicament for reducing fat accumulation in the liver of a human for the treatment of NAFLD and/or NASH. In one embodiment of this aspect, the SGLT-2 inhibitor is selected from dapagliflozin, canagliflozin, remogliflozin etabonate, ipragliflozin and empagliflozin; for example dapagliflozin.

In a further aspect, there is provided the use of a combination of an SGLT-2 inhibitor with an icosapent ethyl product, such as Vascepa® or a bioequivalent version thereof, in the manufacture of a medicament for reducing fat accumulation in the liver of a human for the treatment of NAFLD and/or NASH.

In a further aspect, there is provided the use of a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these, in the manufacture of a medicament for reducing fat accumulation in the liver of a human for the treatment of NAFLD and/or NASH.

In a further aspect, there is provided the use of a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, in the manufacture of a medicament for reducing fat accumulation in the liver of a human for the treatment of NAFLD and/or NASH.

In a further aspect, there is provided the use of a combination of dapagliflozin with an OM3-EE product, such as Lovaza® or Omtryg® or a bioequivalent version of any of these, in the manufacture of a medicament for reducing fat accumulation in the liver of a human for the treatment of NAFLD and/or NASH.

In a further aspect, there is provided the use of a combination of dapagliflozin with an icosapent ethyl product, such as Vascepa® or a bioequivalent version thereof, in the manufacture of a medicament for reducing fat accumulation in the liver of a human for the treatment of NAFLD and/or NASH.

In a further aspect, there is provided the use of a combination of an SGLT-2 inhibitor and an OM3-CA composition in the manufacture of a medicament for reducing fat accumulation in the liver of a human for the treatment of NAFLD and/or NASH.

In a further aspect, there is provided the use of a combination of dapagliflozin and an OM3-CA composition in the manufacture of a medicament for reducing fat accumulation in the liver of a human for the treatment of NAFLD and/or NASH.

In a further aspect, there is provided the use of a combination of dapagliflozin and Epanova® in the manufacture of a medicament for reducing fat accumulation in the liver of a human for the treatment of NAFLD and/or NASH.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH, wherein the subject is non diabetic or diabetic.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH on the basis of NAFLD Activity Score, optionally in combination with a fibrosis stage score.

In a further aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH on the basis of NAFLD Activity Score, optionally in combination with a fibrosis stage score.

In a further aspect, there is provided the use of a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH on the basis of NAFLD Activity Score, optionally in combination with a fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided the use of a combination of an effective dose of Epanova® or a bioequivalent version thereof and an effective dose of dapagliflozin, in the manufacture of a medicament for the treatment of NASH in a subject having, or suspected of having NASH on the basis of NAFLD Activity Score, optionally in combination with a fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH on the basis of the subject's steatosis score, lobular inflammation score and ballooning score, optionally in combination with the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH in a subject having, or suspected of having NASH, wherein the subject has normal or substantially normal biliary tract function. In one aspect a normal or substantially normal biliary tract function is determined on the basis of the subject's alkaline phosphatase (ALP) and bilirubin levels.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH; administering the combination; and thereby improving the steatosis, ballooning and/or lobular inflammation condition of said subject, with no worsening of the subject's fibrosis stage score.

In a further aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH; administering the combination; and thereby improving the steatosis, ballooning and/or lobular inflammation condition of said subject, with no worsening of the subject's fibrosis stage score.

In a further aspect, there is provided the use of a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH; administering the combination; and thereby improving the steatosis, ballooning and/or lobular inflammation condition of said subject, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided the use of a combination of an effective dose of Epanova® or a bio-equivalent version thereof and an effective dose of dapagliflozin, in the manufacture of a medicament for the treatment of NASH wherein the treatment comprises: selecting a subject having, or suspected of having NASH; administering the combination; and thereby improving the steatosis, ballooning and/or lobular inflammation condition of said subject, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH on the basis of their NAFLD Activity Score; administering the combination; and thereby improving the NAFLD Activity Score of said subject by at least 1 point, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH on the basis of their NAFLD Activity Score; administering the combination; and thereby improving the NAFLD Activity Score of said subject by at least 2 points, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having, or suspected of having NASH on the basis of their NAFLD Activity Score; administering the combination; and thereby improving the steatosis score of said subject by at least 1 point, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises: selecting a subject having a NAFLD Activity Score greater than or equal to 5; administering the combination; and thereby improving the NAFLD Activity Score of said subject by at least 1 point, with no worsening of the subject's fibrosis stage score.

In a further aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:

selecting a subject having a NAFLD Activity Score greater than or equal to 5;
administering the combination; and thereby improving the NAFLD Activity Score of said subject by at least 1 point, with no worsening of the subject's fibrosis stage score.

In a further aspect, there is provided the use of a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the NAFLD Activity Score of said subject by at least 1 point, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided the use of a combination of an effective dose of Epanova® or a bioequivalent version thereof and an effective dose of dapagliflozin, in the manufacture of a medicament for the treatment of NASH, wherein the treatment comprises:
selecting a subject, previously diagnosed with Type II diabetes mellitus, having a NAFLD Activity Score greater than or equal to 5;
administering the combination; and thereby improving the NAFLD Activity Score of said subject by at least 1 point, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the NAFLD Activity Score of said subject by at least 2 points, with no worsening of the subject's fibrosis stage score.

In a further aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the NAFLD Activity Score of said subject by at least 2 points, with no worsening of the subject's fibrosis stage score.

In a further aspect, there is provided the use of a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the NAFLD Activity Score of said subject by at least 2 points, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided the use of a combination of an effective dose of Epanova® or a bioequivalent version thereof and an effective dose of dapagliflozin, in the manufacture of a medicament for the treatment of NASH, wherein the treatment comprises:
selecting a subject, previously diagnosed with Type II diabetes mellitus, having a NAFLD Activity Score greater than or equal to 5;
administering the combination; and thereby improving the NAFLD Activity Score of said subject by at least 2 points, with no worsening of the subject's fibrosis stage score.

In a further aspect, there is provided the use of a combination of an effective dose of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture a medicament for the treatment of NASH wherein the treatment comprises:
selecting a subject having a NAFLD Activity Score greater than or equal to 5;
administering the combination; and thereby improving the steatosis score of said subject by at least 1 point, with no worsening of the subject's fibrosis stage score.

In a further aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the steatosis score of said subject by at least 1 point, with no worsening of the subject's fibrosis stage score.

In a further aspect, there is provided the use of a combination of an effective dose of an OM3-CA product, such as Epanova® or a bioequivalent version thereof and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
administering the combination; and thereby improving the improving the steatosis score of the subject by at least 1 point, with no worsening of the subject's fibrosis stage score. Suitably in this aspect, the SGLT-2 inhibitor is selected from dapagliflozin, canagliflozin, remogliflozin etabonate, ipragliflozin and empagliflozin. In one embodiment of this aspect the SGLT-2 inhibitor is dapagliflozin. In one embodiment of this aspect, the subject in need of treatment has been diagnosed with Type II diabetes mellitus.

In a further aspect, there is provided the use of a combination of an effective dose of Epanova® or a bioequivalent version thereof and an effective dose of dapagliflozin, in the manufacture of a medicament for the treatment of NASH, wherein the treatment comprises:
selecting a subject, previously diagnosed with Type II diabetes mellitus, having a NAFLD Activity Score greater than or equal to 5;
administering the combination; and thereby improving the steatosis score of the subject by at least 1 point, with no worsening of the subject's fibrosis stage score.

In a further aspect, there is provided the use of a combination of an omega-3 fatty acid composition (wherein the omega-3 fatty acid composition contains one or more omega-3 fatty acids which may be present as acids, esters, triglycerides, phospholipids or salts) and an effective dose of an SGLT-2 inhibitor or a pharmaceutically acceptable salt thereof, a stereoisomer thereof, or a prodrug ester thereof, in the manufacture of a medicament for the treatment of NASH wherein the treatment comprises:
selecting a subject having a NAFLD Activity Score greater than or equal to 5;
determining the subject's ALP and bilirubin serum levels;
administering the combination; and thereby improving the steatosis condition of said subject, with no worsening of the subject's fibrosis stage score.

In some aspects, selecting a subject having or suspected of having NAFLD and/or NASH comprises selecting a subject having a NAFLD Activity Score greater than or equal to 5; or steatosis score equal or greater than 1; or lobular inflammation score equal to or greater than 1; or ballooning score equal to or greater than 1; or fibrosis score equal to or greater than 1.

In a particular aspect, treatment with the omega-3 fatty acid composition and the SGLT-2 inhibitor is particularly effective at improving the subject's steatosis score, and so particularly effective at reducing liver fat.

Therefore in one aspect, there is provided the use of a combination of an effective dose of an OM3-CA composition and an effective dose of an SGLT-2 inhibitor or a pharmaceutically acceptable salt thereof, a stereoisomer thereof, or a prodrug ester thereof in the manufacture of a medicament for the reduction of liver fat in a subject comprising selecting a subject who has been diagnosed with Type II diabetes mellitus and diagnosed as having raised liver fat (>5.5% as assessed by MRI or MRS); administering the combination; and thereby reducing the liver fat content by at least 15%, such as at least 20%, such as at least 25% (as assessed by MRI or MRS).

In one aspect, there is provided the use of a combination of an effective dose of Epanova® or a bioequivalent version thereof and an effective dose of dapagliflozin in the manufacture of a medicament for the reduction of liver fat in a subject comprising selecting a subject who has been diagnosed with Type II diabetes mellitus and diagnosed as having raised liver fat (>5.5% as assessed by MRI or MRS); administering the combination; and thereby reducing the liver fat content by at least 15%, such as at least 20%, such as at least 25% (as assessed by MRI or MRS).

In one aspect, there is provided the use of a combination of an effective dose of Epanova® or a bioequivalent version thereof and an effective dose of dapagliflozin, in the manufacture of a medicament for the reduction of liver fat in a subject who has been diagnosed with Type II diabetes mellitus and diagnosed as having raised liver fat (>5.5% as assessed by MRI or MRS).

In one aspect, there is provided the use of a combination of an effective dose of Epanova® or a bioequivalent version thereof and an effective dose of dapagliflozin, in the manufacture of a medicament for the reduction of liver fat and reduction in plasma triglyceride level, in a subject who has been diagnosed with Type II diabetes mellitus and diagnosed as having raised liver fat (>5.5% as assessed by MRI or MRS).

In one aspect, there is provided the use of a combination of an effective dose of Epanova® or a bioequivalent version thereof and an effective dose of dapagliflozin, in the manufacture of a medicament for the reduction of liver fat and raising of plasma EPA and/or DHA levels, in a subject who has been diagnosed with Type II diabetes mellitus and diagnosed as having raised liver fat (>5.5% as assessed by MRI or MRS).

In another aspect, there is provided the use of a combination of an effective dose of Epanova® or a bioequivalent version thereof and an effective dose of dapagliflozin, in the manufacture of a medicament for the reduction of liver fat and the reduction of cell death and/or ballooning, in a subject who has been diagnosed with Type II diabetes mellitus and diagnosed as having raised liver fat (>5.5% as assessed by MRI or MRS).

In another aspect, there is provided the use of a combination of an effective dose of Epanova® or a bioequivalent version thereof and an effective dose of dapagliflozin in the manufacture of a medicament for use in the reduction of liver fat and the reduction of liver inflammation, in a subject in need thereof.

In one aspect, there is provided the use of a combination of an effective dose of Epanova® or a bioequivalent version thereof and an effective dose of dapagliflozin in the manufacture of a medicament for use in the reduction of liver fat in a subject who is overweight (with a BMI of >25), has been diagnosed as having raised liver fat (>5.5% as assessed by MRI or MRS) and optionally has also been diagnosed with Type II diabetes mellitus.

In one aspect, there is provided the use of a combination of an effective dose of Epanova® or a bioequivalent version thereof and an effective dose of dapagliflozin in the manufacture of a medicament for use in the reduction of liver fat and reduction in plasma triglyceride level, in a subject who is overweight (with a BMI of >25), who has been diagnosed as having raised liver fat (>5.5% as assessed by MRI or MRS), and optionally has also been diagnosed with Type II diabetes mellitus.

In one aspect, there is provided the use of a combination of an effective dose of Epanova® or a bioequivalent version thereof and an effective dose of dapagliflozin in the manufacture of a medicament for use in the reduction of liver fat and increase of plasma EPA and/or DHA levels, in a subject who is overweight (with a BMI of >25), has been diagnosed as having raised liver fat (>5.5% as assessed by MRI or MRS) and optionally has also been diagnosed with Type II diabetes mellitus.

In another aspect, there is provided the use of a combination of an effective dose of Epanova® or a bioequivalent version thereof and an effective dose of dapagliflozin in the manufacture of a medicament for use in the reduction of liver fat and the reduction of hepatic cell death and/or ballooning, in a subject who is overweight (with a BMI of >25), has been diagnosed as having raised liver fat (>5.5% as assessed by MRI or MRS) and optionally has also been diagnosed with Type II diabetes mellitus.

In another aspect, there is provided the use of a combination of an effective dose of Epanova® or a bioequivalent version thereof and an effective dose of dapagliflozin in the manufacture of a medicament for use in halting progression of liver fibrosis, in a subject in need thereof.

In another aspect, there is provided the use of a combination of an effective dose of Epanova® or a bioequivalent version thereof and an effective dose of dapagliflozin, in a subject who has been diagnosed with NAFLD or NASH, in the manufacture of a medicament for use in halting progression of NAFLD and/or NASH, said treatment comprising administering the combination and thereby causing a halt in progression of fibrosis of the subject's liver.

In another aspect there is provided the use of a combination of an effective dose of Epanova® or a bioequivalent version thereof and an effective dose of dapagliflozin in the manufacture of a medicament for use in the treatment of NASH, in a subject having, or suspected of having NASH, said treatment comprising administering the combination and thereby causing a reduction in body weight of the subject.

In another aspect there is provided the use of a combination of an effective dose of Epanova® or a bioequivalent version thereof and an effective dose of dapagliflozin in the manufacture of a medicament for use in the treatment of NASH, in a subject having, or suspected of having NASH, said treatment comprising administering the combination and thereby causing an increase in insulin sensitisation of the subject.

In some embodiments, the subject shows unobstructed or normal excretion of bile, does not suffer from injury in the liver, does not exhibit liver dysfunction, shows normal levels of direct bilirubin, does not possess biliary tract disease or the subject possesses biliary tract disease in an early stage.

In some embodiments, the subject does not have a condition selected from the group consisting of alcoholic liver injury, drug-induced liver injury, chronic active hepatitis, cirrhosis and liver cancer.

In some aspects, the subject does not have a familial history of fatty liver disease.

In other aspects, the subject has one or more genetic polymorphisms associated with increased risk of fatty liver disease.

In other aspects, the subject has a familial history of fatty liver disease.

In some aspects, a patient is diagnosed as having NASH on the basis of histopathological diagnosis of definitive NASH.

In another aspect there is provided the use of a combination of an effective dose of Epanova® or a bioequivalent version thereof and an effective dose of dapagliflozin in the manufacture of a medicament for use in the reversal or resolution of NASH, in a subject having NASH, wherein the NASH status of the subject is diagnosed by histopathological assessment.

In one aspect, the humans to be treated with the above combinations of omega-3 fatty acid compositions and SGLT-2 inhibitors have been diagnosed as suffering from Type II diabetes (in addition to NAFLD and/or NASH). In another aspect, the humans to be treated with the above combinations have not been diagnosed as suffering from Type II diabetes. In a further aspect, the humans to be treated with the above combinations are those that do not exhibit symptoms of diabetes and have a plasma glucose level below 11.1 mmol/L, have a fasting plasma glucose level below 7 mmol/L; or have a two-hour plasma glucose level of below 11.1 mmol/L during an oral glucose tolerance test.

In one aspect, the humans to be treated with the above combinations of omega-3 fatty acid compositions and SGLT-2 inhibitors suffer from pancreatic exocrine insufficiency (in addition to NAFLD and/or NASH). In a further aspect, the humans to be treated suffer from pancreatic exocrine insufficiency, and Type II diabetes (in addition to NAFLD and/or NASH). In a particular embodiment of these aspects, the omega-3 fatty acid composition to be used is an OM3-CA composition, such as provided as Epanova® or bio-equivalent versions thereof.

In one aspect, the humans to be treated with the above combinations of omega-3 fatty acid compositions and SGLT-2 inhibitors have been diagnosed as suffering from pancreatic exocrine insufficiency (in addition to NASH), for example by use of an FEC test. In a further aspect, the humans to be treated have been diagnosed as suffering from pancreatic exocrine insufficiency for example by use of an FEC test, and also suffer from Type II diabetes (in addition to NASH). In a particular embodiment of these aspects, the omega-3 fatty acid composition to be used is an OM3-CA composition, such as provided as Epanova® or bio-equivalent versions thereof.

In the above aspects (combinations, uses and methods) conveniently the SGLT-2 inhibitor and omega-3 fatty acid composition are each present in unit dosage forms. Conveniently, the SGLT-2 inhibitor is in the form of a tablet, at a dosage level known in the art to be a suitable dose (for example a dose approved by a regulatory body for the treatment of diabetes). Conveniently the omega-3 fatty acid composition is in the form of an oil and is formulated in one or more capsules, such as hard or soft gelatin capsules as described hereinbefore, and at a dosage level known in the art, for example, about 1 to 4 g, particularly 2 to 4 g, of omega-3 fatty acid composition. Conveniently, the omega-3 fatty acid composition is formulated into capsules each of which contain approximately one gram of active ingredient, so that multiple capsules are administered to obtain the required dose.

In the above combinations, combinations for use, uses and methods, an effective dose of dapagliflozin should be understood to mean any dose approved for marketing by a Regulatory Authority (such as the US FDA), such as 5 mg or 10 mg.

In the above combinations, combinations for use, uses and methods, an effective dose of Epanova® should be understood to mean 1 g, 2 g, or 4 g, particularly the doses of 2 g and 4 g approved by the US FDA and more particularly 4 g.

In a further aspect, there is provided a kit of parts comprising
a) a unit dosage form comprising an SGLT-2 inhibitor or a pharmaceutically acceptable salt thereof, a stereoisomer thereof, or a prodrug ester thereof;
b) a unit dosage form comprising an omega-3 fatty acid composition (wherein the omega-3 fatty acid composition comprises one or more omega-3 fatty acids which may be present as acids, esters, triglycerides, phospholipids or salts); and, optionally,
c) instructions for use in the treatment of NAFLD and/or NASH.

In a further aspect, there is provided a kit of parts comprising
a) a unit dosage form comprising an SGLT-2 inhibitor;
b) a unit dosage form comprising an OM3-CA, such as Epanova® or a bioequivalent version thereof and, optionally,
c) instructions for use in the treatment of NAFLD and/or NASH.

In a further aspect, there is provided a kit of parts comprising
a) a unit dosage form comprising an SGLT-2 inhibitor selected from dapagliflozin, canagliflozin, remogliflozin etabonate, ipragliflozin and empagliflozin;
b) a unit dosage form comprising an OM3-CA, such as Epanova® or a bioequivalent version thereof; and, optionally, c) instructions for use in the treatment of NAFLD and/or NASH.

In a further aspect, there is provided a kit of parts comprising
a) a unit dosage form comprising dapagliflozin;
b) a unit dosage form comprising an OM3-CA, such as Epanova® or a bioequivalent version thereof; and, optionally,
c) instructions for use in the treatment of NAFLD and/or NASH.

In a further aspect, there is provided a kit of parts comprising
a) a unit dosage form comprising an SGLT-2 inhibitor;
b) a unit dosage form comprising an OM3-EE, such as Lovaza® or Omtryg® or a bioequivalent version of any of these; and, optionally,
c) instructions for use in the treatment of NAFLD and/or NASH.

In a further aspect, there is provided a kit of parts comprising
a) a unit dosage form comprising an SGLT-2 inhibitor selected from dapagliflozin, canagliflozin, remogliflozin etabonate, ipragliflozin and empagliflozin;
b) a unit dosage form comprising an OM3-EE, such as Lovaza® or Omtryg® or a bioequivalent version of any of these; and, optionally,
c) instructions for use in the treatment of NAFLD and/or NASH.

In a further aspect, there is provided a kit of parts comprising
a) a unit dosage form comprising dapagliflozin;
b) a unit dosage form comprising an OM3-EE, such as Lovaza® or Omtryg® or a bioequivalent version of any of these; and, optionally,
c) instructions for use in the treatment of NAFLD and/or NASH.

In a further aspect, there is provided a kit of parts comprising
a) a unit dosage form comprising an SGLT-2 inhibitor;
b) a unit dosage form comprising icosapent ethyl, such as Vascepa® or a bioequivalent version thereof; and, optionally,
c) instructions for use in the treatment of NAFLD and/or NASH.

In a further aspect, there is provided a kit of parts comprising
a) a unit dosage form comprising an SGLT-2 inhibitor selected from dapagliflozin, canagliflozin, remogliflozin etabonate, ipragliflozin and empagliflozin;
b) a unit dosage form comprising icosapent ethyl, such as Vascepa® or a bioequivalent version thereof; and, optionally,
c) instructions for use in the treatment of NAFLD and/or NASH.

In a further aspect, there is provided a kit of parts comprising
a) a unit dosage form comprising dapagliflozin;
b) a unit dosage form comprising icosapent ethyl, such as Vascepa® or a bioequivalent version thereof; and, optionally,
c) instructions for use in the treatment of NAFLD and/or NASH.

In another aspect, the results from analysis of the secondary variables in the Effect II study as described in Examples 1, 1A and 1B, indicate that the combination of Epanova® and dapagliflozin is effective at treating NASH.

Combination with Further Agents

Patients with cardiovascular conditions such as NAFLD and/or NASH may need medication in addition to the combination of the invention. For example, one or more additional agents for improving glycemic control (ie anti-diabetic agent) may be required. In another example, an additional agent for controlling lipid levels, such as a statin or other lipid reducing agent, may be required.

Therefore in a further aspect there is provided a combination of an SLGT-2 inhibitor with an omega-3 fatty acid composition (wherein the omega-3 fatty acid composition comprises one or more omega-3 fatty acids which may be present as acids, esters, phospholipids or salts) and an additional anti-diabetic agent and/or an additional agent for controlling lipid levels.

In a further aspect, there is provided a combination of an SGLT-2 inhibitor with an OM3-CA and an additional anti-diabetic agent and/or an additional agent for controlling lipid levels.

In a further aspect, there is provided a combination of dapagliflozin with an OM3-CA and an additional anti-diabetic agent and/or an additional agent for controlling lipid levels.

In a further aspect, there is provided a combination of dapagliflozin with Epanova® or a bio-equivalent version thereof, and an additional anti-diabetic agent and/or an additional agent for controlling lipid levels.

In a further aspect, there is provided a combination of an SGLT-2 inhibitor with an OM3-EE product, such as Lovaza® or Omtryg® or a bioequivalent version of any of these, and an additional anti-diabetic agent and/or an additional agent for controlling lipid levels.

In a further aspect, there is provided a combination of an SGLT-2 inhibitor with icosapent ethyl, such as Vascepa® or a bioequivalent version thereof, and an additional anti-diabetic agent and/or an additional agent for controlling lipid levels.

In a further aspect, there is provided a combination of an SGLT-2 inhibitor selected from dapagliflozin, canagliflozin, remogliflozin etabonate, ipragliflozin and empagliflozin with an OM3-EE product, such as Lovaza® or Omtryg® or a bioequivalent version of any of these and an additional anti-diabetic agent and/or an additional agent for controlling lipid levels.

In a further aspect, there is provided a combination of an SGLT-2 inhibitor selected from dapagliflozin, canagliflozin, remogliflozin etabonate, ipragliflozin and empagliflozin with an icosapent ethyl product, such as Vascepa® or a bioequivalent version thereof, and an additional anti-diabetic agent and/or an additional agent for controlling lipid levels.

In a further aspect, there is provided a combination of dapagliflozin with an OM3-EE product, such as Lovaza® or Omtryg® or a bioequivalent version of any of these and an additional anti-diabetic agent and/or an additional agent for controlling lipid levels.

In a further aspect, there is provided a combination of dapagliflozin with an icosapent ethyl product, such as Vascepa® or a bioequivalent version thereof, and an additional anti-diabetic agent and/or an additional agent for controlling lipid levels.

Such further combinations may suitably be used in the methods of treatments and uses described above.

Examples of suitable additional anti-diabetic agents for use in co-administration of the present invention include, but are not limited to, biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) and other agonists of the GLP-1 receptor.

Other suitable thiazolidinediones include, but are not limited to, MCC-555 (disclosed in U.S. Pat. No. 5,594,016, Mitsubishi), faraglitazar (GI-262570, Glaxo-Wellcome), englitazone (CP-68722, Pfizer), darglitazone (CP-86325, Pfizer); isaglitazone (MIT/Johnson& Johnson), reglitazar OTT-501, (JPNT/Pharmacia & Upjohn), rivoglitazone (R-119702, Sankyo/WL), liraglutide (NN-2344, Dr. Reddy/NN), and (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include, but are not limited to, muraglitazar, peliglitazar, tesaglitazar AR-H039242 (AstraZeneca), GW-501516 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998); WO 01/21602 and in U.S. Pat. No. 6,414,002 and U.S. Pat. No. 6,653,314, the disclosures of which are incorporated herein by reference in their entireties, employing dosages as set out therein. In one embodiment, the compounds designated as preferred in the cited references are preferred for use herein.

Suitable aP2 inhibitors include, but are not limited to, those disclosed in U.S. application Ser. No. 09/391,053, filed Sep. 7, 1999, and in U.S. Pat. No. 6,548,529, the disclosures of which are incorporated herein by reference in their entireties, employing dosages as set out therein.

Other suitable meglitinides include nateglinide (Novartis) or KAD 1229 (PF/Kissei).

In another embodiment, the present invention further provides for the co-administration of one or more additional anti-diabetic agents, wherein the additional anti-diabetic agent is metformin.

In a further aspect of the invention, there is provided a combination of an omega-3 fatty acid composition (particularly provided as Epanova®), dapagliflozin and saxagliptin, suitably for the treatment of NASH.

Suitable lipid-lowering agents include HMG-CoA reductase inhibitors, also known as statins. Examples of suitable statins include rosuvastatin, simvastatin, fluvastatin, pravastatin, atorvastatin and pitavastatin.

Other suitable lipid-lowering agents include PPAR α-agonists (fibrates, eg gemfibrozil); bile acid sequestrants (cholestyramine); cholesterol absorption inhibitors (plant stanols, synthetic inhibitors); bile acid absorption inhibitors (IBATi) and nicotinic acid and analogues (niacin and slow release formulations).

Example 1: Epanova® and Dapagliflozin Alone and in Combination on Liver Fat Content in Type 2 diabetiC Patients: A Double-Blind Randomized Placebo-Controlled, Parallel-Group 12 Week Study; EFFECT II List of Abbreviations and Definition of Terms The following abbreviations and special terms are used in this description.

| Abbreviation or special term | Explanation |
| --- | --- |
| AE | Adverse event |
| CRF | Case Report Form (electronic/paper) |
| CSA | Clinical Study Agreement |
| CSR | Clinical Study Report |
| DAE | Discontinuation of Investigational Product due to Adverse Event |
| DNA | Deoxyribonucleic acid |
| EC | Ethics Committee, synonymous to Institutional Review Board (IRB) and Independent Ethics Committee (IEC) |
| GCP | Good Clinical Practice |
| ICH | International Conference on Harmonisation |
| IP | Investigational Product |
| LSLV | Last Subject Last Visit |
| OAE | Other Significant Adverse Event |
| PGx | Pharmacogenetic research |
| PI | Principal Investigator |
| SAE | Serious adverse event |
| WBDC | Web Based Data Capture |

STUDY DRUG (Epanova®)—Type A porcine soft gelatin capsules are prepared, each containing one gram (1 g) of a PUFA composition comprising omega-3 PUFAs in free acid form. The capsules are coated with Eudragit NE 30-D (Evonik Industries AG).

This study is a double-blind randomized placebo-controlled, parallel-group 12 week study to assess the effect of Epanova and dapagliflozin on liver fat in Type 2 diabetics with liver steatosis (≥5.5% as measured with MRI).

The subjects will be randomized 1:1:1:1 to placebo, Epanova 4 g, dapagliflozin 10 mg, or the combination of Epanova 4 g and dapagliflozin 10 mg. The patients will be treated for 12 weeks. Visit at week 7 is for supply of study medication and safety monitoring. Total study length will be maximum 15 weeks and a safety follow-up visit will be held within 1 week after study end.

The study objectives are to explore if the combination of Epanova and dapagliflozin markedly reduce liver fat as well as to explore if there is an interaction between Epanova and dapagliflozin on glucose control. Moreover, the study aim to investigate effects of Epanova and dapagliflozin on other parameters related to liver inflammation and liver cell damage.

The primary aim of this study is to investigate the effect of Epanova and dapagliflozin and the combination of Epanova and dapagliflozin on liver fat content as compared to placebo using MRI.

The secondary aim is to investigate effects on parameters associated with NAFLD status such as plasma levels of transaminases, cytokeratin-18 fragments, glucose, insulin (HOMA-IR), HbA1c, adiponectin, oxidative stress biomarkers (e.g. 13-HODE) as well as inflammatory parameters like hsCRP and osteopontin.

The tertiary aim is to investigate effects on liver fat content in relation to changes in body fat and visceral fat, including pancreatic fat, lipoproteins, especially plasma triglycerides as well as plasma levels of DHA and EPA An exploratory aim of the study is to investigate effects on glucose control (fasting glucose and insulin, oral glucose tolerance and HbA1c) of dapagliflozin alone as compared to the combination with Epanova.

A second exploratory aim is to investigate parameters associated cross-sectionally with liver fat at baseline to build an algorithm that can predict liver steatosis (NAFLD screen study). Two different scores will be developed: 1) a liver steatosis-score for the detection of liver steatosis based on clinically measurable variables. "The GP score". 2) a liver steatosis-score for the detection of liver steatosis based on an extended set of variables, including genetics, metabolomics and proteomics. "The academic score"

Each subject should meet all of the inclusion criteria and none of the exclusion criteria for this study.

For inclusion in the study subjects should fulfill the following criteria:
1. Provision of informed consent prior to any study specific procedures.
2. Men or women≥40 years and ≤75 years with suitable veins for cannulation or repeated venepuncture.
3. Have liver fat content as assessed by MRI≥5.5%.
4. Type 2 diabetes on no glucose lowering therapy or on stable metformin and/or sulfonylurea therapy.
5. Have a body mass index (BMI)≥25 and ≤40 kg/m2.
6. Willingness to maintain current life-style, including activity level.

Subjects should not enter the study if any of the following exclusion criteria are fulfilled:
1. Involvement in the planning and/or conduct of the study (applies to both AstraZeneca staff and/or staff at the study site)
2. Previous enrolment in the present study.
3. Participation in another clinical study with an investigational product during the last 28 days.
4. Any condition when MRI is contraindicated such as, but not limited to, having a pacemaker or claustrophobia.
5. History of or presence of (as found at visit 1) any clinically significant disease or disorder which, in the opinion of the investigator, may either put the subject at risk because of participation in the study, or influence the results or the subject's ability to participate in the study.
6. Any clinically significant illness, medical or surgical procedure or trauma within 4 weeks of the first administration of investigational product.
7. Intolerance to omega-3 fatty acids, ethyl esters or fish.
8. Intolerance or allergy to dapaglifozin or any other SGLT2 inhibitor or any other substance in the tablets.
9. Use of dapagliflozin or any other SGLT2 inhibitor within 4 weeks of visit 1.
10. eGFR<60 mL/min/1.73 $m^2$ at screening. (Modification of Diet in Renal Disease equation (Levey, et al. 1999)
11. Use of insulin or GLP-1 therapy or other OADs than metformin or sulfonylurea.
12. Type 2 diabetics with HbA1c>9% (=86 mmol/mol) or <6.5% (=48 mmol/mol).
13. Use of fish oil, other EPA or DHA containing supplements, or EPA and/or DHA-fortified foods within 6 weeks from visit 1, or during the study.
14. Ongoing weight-loss diet (hypocaloric diet) or use of weight loss agents, unless the diet or treatment has been stopped at least 3 months before screening and that the subject have had a stable body weight (+/−3 kg) during the 3 proceeding months before screening.
15. Use of flaxseed, *perilla* seed, hemp, *spirulina*, or black currant oils within 1 month from study start and during the study until study end.
16. Any clinically significant abnormalities in clinical chemistry, haematology or urinalysis results as judged by the investigator.
17. Elevated NAFLD fibrosis score (≥−1.455) based on the assessment obtained at screening.*)
18. Recent history (past 12 months) of drug abuse or alcohol abuse. Alcohol abuse was be defined as >14 drinks per week (1 drink=35 cl beer, 14 cl wine, or 4 cl hard liquor) or as judged by the investigator.
19. Women who are pregnant, lactating, or planning to become pregnant during the study period, or women of childbearing potential who are not using acceptable contraceptive methods. A woman is considered of childbearing potential if she is not surgically sterile or is less than 1 year since last menstrual period.
20. Any other condition the investigator believe would interfere with the subject's ability to provide informed consent, comply with study instructions, or which might confound the interpretation of the study results or put the subject at undue risk.
21. Plasma donation within one month of screening or any blood donation/blood loss>500 mL during the 3 months prior to visit 1 or during the study.

*) On-line score calculator: http://nafldscore.com/
<−1.455: predictor of absence of significant fibrosis (F0-F2 fibrosis)
≤−1.455 to ≤0.675: indeterminate score
>0.675: predictor of presence of significant fibrosis (F3-F4 fibrosis))

The screening visit (visit 1) will be made up to 14 days before randomization (visit 2). At screening, consenting subjects are assessed to ensure that they meet eligibility criteria initially. Subjects who do not meet these criteria must not be enrolled in the study.

The amount of assessment made at this visit are extensive and includes consent procedures, medical history including demographics, clinical assessment, MRI, oral glucose tolerance testing (OGTT), and sampling as noted in Study Plan. Potentially, visit 1 has to take place over two days to accomplish logistically MRI, interviews, instructions, informed consent and fasting plasma samples including OGTT.

At visit 2, the results of the screening assessments will be evaluated to assure that the patient meet the eligibility criteria. Once these are met, the patient will be randomised and the study drug will be administered. At this visit, sampling as noted in Study Plan will be made. The patients will then be treated for 12 weeks.

The patient will return to the clinic 6 weeks after start of treatment (visit 3) for supply of study drug. At this visit, safety monitoring is made (including registration of AEs and sampling).

Additional 6 weeks later the treatment will be stopped and the patient will return to the clinic (visit 4). At this visit, safety monitoring is made (including registration of AEs and sampling as noted in Study Plan). Additionally, the visit will include clinical assessment, MRI, oral glucose tolerance testing (OGTT), and efficacy sampling.

Within 1 week after visit 4, a safety follow-up contact via telephone (visit 5).

Potential AEs will be registered. If any laboratory safety signals have been observed and not resolved during the study, the visit need to be made at the clinic and extra safety samples will be taken in order to follow-up on these signals. An additional later time-point may be chosen.

The patients will undergo a MRI-scanning at visit 1 (screen) and at visit 4 (stop treatment).

The primary aim is to investigate liver fat using Magnetic Resonance Imaging (MRI). MRI using Dixon based techniques is used since it has a higher precision than Magnetic Resonance Spectroscopy (MRS) to assess liver fat content. The primary variable is liver fat (%) calculated as: liver fat*100/(liver fat+liver water). Also liver volumes will be measured to investigate the total liver fat content: total liver fat (1)=liver fat (%)*liver volume.

Omega-3 FA (Kabir et al, Am J Clinical Nutrition, 2007, 86, 1670-1679) and dapagliflozin (Bolinder et al, Journal of clinical Endocrinology and Metabolism, 2012, 97, 1020-1031; Bolinder et al, Diabetes, Obesity and Metabolism, 2014, 16, 159-169) treatment have each been shown to reduce body fat content. Therefore, whole body MRI will be performed to assess total fat mass and lean tissue. Pancreatic lipid content (%) and size will also be measured. Also visceral fat mass and subcutaneous fat volumes using MRI will be assessed from Dixon based MRI techniques. Imaging will be performed in the abdominal region using the L4/L5 interface as the anatomical reference. Visceral and subcutaneous fat volumes will be given in liters.

All investigations will be performed on a clinical MRI scanner at 1.5 T field strength with the patients in the supine position.

Samples to assess lipid- and glucose-parameters will be taken at visit 1 (screen), visit 2 (randomisation) and visit 4 (stop treatment) respectively. The plasma levels of insulin, glucose and NEFA will also analysed in connection with the oral glucose tolerance test (OGTT).

Samples to assess lipids, lipid absorption and oxidative stress will be taken at visit 1 (screen) and visit 4 (stop treatment).

Samples to assess inflammation, oxidative stress, choline metabolism and cell death will be taken at visit 1 (screen) and visit 4 (stop treatment).

Samples to assess Metabolomics and proteomics will be taken at visit 1 (screen) only.

Samples to assess iron-parameters and Vitamin D will be taken at visit 1 (screen) only.

Oral glucose tolerance test (OGTT) will be done at Visit 1 and 4. All plasma samples will be taken from a catheter inserted into an anticubital vein.

A physical examination will be performed and include an assessment of the following: general appearance, respiratory, cardiovascular and abdomen.

Single doses of 4 g Epanova and 10 mg dapagliflozin will be used.

Randomisation will be made in a 1:1:1:1-fashion and thus will:
  ¼ of the population receive Epanova 4 g once daily
  ¼ of the population receive dapagliflozin 10 mg once daily
  ¼ of the population receive both Epanova 4 g once daily and dapagliflozin 10 mg once daily
  ¼ of the population receive placebo capsules and tablets.

All medication is taken once daily in the morning.

The primary outcome variable of liver fat content will be analyzed on the log-scale using a linear mixed effects model with treatment and time as fixed effects and patient as a random effect. Resulting differences in log (liver fat content) will be back-transformed to the geometric mean ratio and presented as the difference in mean percent change from baseline along with a 95% confidence interval (CI) and associated p value. To meet the primary objective of evaluating the effect of the combination of Epanova and dapagliflozin compared to both its components Dunnett's statistical testing strategy to control the family-wise type-1 error at 5% will be employed. No adjustment for multiplicity will be made for the secondary, tertiary, and exploratory endpoints.

For the secondary and tertiary endpoints a similar statistical analysis will be performed. For variables that are approximately normally distributed the data will be analyzed on the original scale and the results will be presented as the absolute difference in mean change from baseline. The distribution of the different variables will determine whether or not a transformation of the data will be performed prior to analysis.

Sensitivity analyses of the primary endpoint will be performed to evaluate the effect of any missing data.

Example 1b

In a variation of the above protocol, EFFECT II may be carried out as described in Example 1 above but with the following amendments (with remaining details being as described above).

Primary Objective
The primary aim of this study is to evaluate the efficacy of the combination of Epanova® and dapagliflozin as compared to placebo with respect to reduction in liver fat content (%) at the end of 12 weeks of double-blind treatment in Type 2 diabetics with increased liver fat content as defined by >5.5% (assessed by MRI).

Secondary Objective
The secondary aim of this study is to evaluate the relative efficacy between combination of Epanova® and dapagliflozin, Epanova® alone, dapagliflozin alone and placebo with respect to reduction in liver fat at the end of 12 weeks of double-blind treatment in Type 2 diabetics with increased liver fat content as defined by >5.5% (assessed by MRI).

Exploratory Objectives
An exploratory aim is to evaluate the effect of the combination of Epanova® and dapagliflozin, Epanova® alone, and dapagliflozin alone compared to placebo on liver associated parameters indicating oxidative stress, and inflammation and/or cell death.

An exploratory aim is to evaluate the effects of the combination of Epanova and dapagliflozin, Epanova alone, and dapagliflozin alone compared to placebo on body fat depots (e.g. visceral and subcutaneous fat and pancreatic fat content (%)), fluid diffusion in the liver, plasma levels of lipids, lipoproteins and total DHA and EPA.

An exploratory aim of the study is to investigate the effects on glucose control (e.g. fasting glucose and HbA1c) of dapagliflozin and Epanova® in combination, Epanova® alone, and dapagliflozin alone as compared to placebo.

An exploratory aim is to investigate changes in plasma fatty acid composition and increases in DHA and EPA to treatment effect on liver fat and plasma triglycerides.

An exploratory aim is to analyse genetic polymorphisms in relation to liver fat accumulation.

Another exploratory aim is to build an algorithm that can predict fatty liver based on cross-sectional data ("NAFLD screen study").

Inclusion Criteria
For inclusion in the study patients should fulfil the following criteria:
1. Provision of informed consent prior to any study specific procedures.
2. Men or women≥40 years and ≤75 years with suitable veins for cannulation or repeated venepuncture.
3. Have liver fat content as assessed by MRI>5.5%.
4. Type 2 diabetes diagnosed since at least 6 months in accordance with WHO criteria. Diagnosis of Type 2 diabetes can be based on the following:
   Prior documentation in medical records of type 2 diabetes AND/OR
   Treatment with anti-hyperglycemic medications and/or diet AND/OR Random plasma glucose≥11.1 mmol/L or fasting≥7.0 mmol/L or HbA1c≥48 mmol/mol (6.5%).
5. Antidiabetic therapy: stable (i.e. >1 months) metformin and/or sulfonylurea or non-pharmacological treatment.
6. For patients without concomitant sulfonylurea: HbA1c≥48 and ≥80 mmol/mol (≥6.5% and ≤9.5%) at visit 1. For patients with concomitant sulfonylurea: HbA1c≥53 and ≤80 mmol/mol (≥7.0% and ≤9.5%) at visit 1.
7. Have a body mass index (BMI)≥25 and ≤40 kg/m2

Exclusion Criteria

Patients should not enter the study if any of the following exclusion criteria are fulfilled:
8. Involvement in the planning and/or conduct of the study (applies to both AstraZeneca staff and/or staff at the study site)
9. Previously randomized in the present study
10. Participation in another clinical study with an investigational product during the last 28 days.
11. Any condition when MRI is contraindicated such as, but not limited to, having a pacemaker or claustrophobia.
12. History of or presence of (as found at visit 1) any clinically significant disease or disorder which, in the opinion of the investigator, may either put the patient at risk because of participation in the study, or influence the results or the patient's ability to participate in the study.
13. Diagnosis or signs of Type 1 diabetes (e.g. history of positive islet antibodies)
14. Creatinine clearance<60 mL/min at screening (Cockcroft-Gault formula).
15. Severe hepatic injury and/or significant abnormal liver function defined as aspartate aminotransferase (AST)>3× upper limit of normal (ULN) and/or alanine aminotransferase (ALT)>3×ULN
16. Total bilirubin>2.0 mg/dL (34.2 μmol/L)
17. Intolerance to omega-3 fatty acids, ethyl esters or fish.
18. Intolerance or allergy to dapaglifozin or any other SGLT2 inhibitor or any other substance in the tablets.
19. Use of dapagliflozin or any other SGLT2 inhibitor within the last 4 weeks prior to visit 1.
20. Use of insulin or GLP-1 therapy or other oral antidiabetics (OADs) than metformin or sulfonylurea within the last 4 weeks prior to visit 1.
21. Use of fish oil, other EPA or DHA containing supplements, or EPA and/or DHA-fortified foods within 4 weeks from visit 1, or during the study.
22. Ongoing weight-loss diet (hypocaloric diet) or use of weight loss agents, unless the diet or treatment has been stopped at least 3 months before screening and that the patient have had a stable body weight (+/−3 kg) during the 3 proceeding months before screening.
23. Use of flaxseed-, *perilla* seed-, hemp-, *spirulina*-, or black currant-oils within 1 month from study start and during the study until study end.
24. Any clinically significant abnormalities in clinical chemistry, hematology or urinalysis results as judged by the investigator. This includes signs of liver disease other than NAFLD that motivates further investigations or treatment based on clinical judgement.
25. Recent history (past 12 months) of drug abuse or alcohol abuse. Alcohol abuse is defined as >14 drinks per week (1 drink=35 cl beer, 14 cl wine, or 4 cl hard liquor) or as judged by the investigator.
26. Women who are pregnant, lactating, or planning to become pregnant during the study period, or women of childbearing potential who are not using acceptable contraceptive methods. A woman is considered of childbearing potential if she is not surgically sterile or is less than 1 year since last menstrual period. Acceptable contraceptive methods are: combined (estrogen and progesterone containing) hormonal contraception associated with inhibition of ovulation (oral, intravaginal, transdermal), progesterone-only hormonal contraception associated with inhibition of ovulation (oral, injectable, implantable), intrauterine device, intrauterine hormone-releasing system, bilateral tubal occlusion and vasectomised partner.
27. Any other condition the investigator believe would interfere with the patient's ability to provide informed consent, comply with study instructions, or which might confound the interpretation of the study results or put the patient at undue risk.
28. Plasma donation within one month of screening or any blood donation/blood loss>500 mL during the 3 months prior to visit 1 or during the study.

OGTT test will be carried out at visit 2, not visit 1.

A telephone contact (Visit 3) will be made after the patient has taken the study drug for 14 days to monitor their general status including diabetic parameters to check if there are any signs of hypo- or hyper-glycemia. Subsequent visit numbering is therefore increased by 1 in comparison to the protocol details given above.

The primary hypotheses are three pairwise comparisons against placebo with respect to liver fat reduction (%). Specifically the following hypotheses will be tested simultaneously:

$H_{0CP}: \mu_C - \mu_P,$ $H_{0EP}: \mu_E - \mu_P,$ $H_{0DP}: \mu_D - \mu_P.$ (C=Epanova+dapagliflozin; D—dapagliflozin; P=placebo; E=Epanova)

The analysis of the primary outcome variable will be performed using the FAS (Full Analysis Set). The primary hypotheses, based on the change from baseline in liver fat—content (%), will be analyzed in the natural-log scale using a linear mixed effects model with treatment and the stratification factor (Baseline liver fat content≤/>8%) as fixed effects, and patient as a random effect terms.

Resulting differences in log (liver fat content) will be back-transformed to the geometric mean ratio and presented as the difference in mean change from baseline along with a 95% confidence interval (CI) and associated p-value.

To meet the primary objective of evaluating the effect of the combination of Epanova and dapagliflozin compared to placebo, a 5% two-sided significance test with a Dunnett alpha adjustment for 3 multiple comparisons will be employed.

The secondary hypotheses are all pairwise comparisons between C, E, D, and P with respect to reduction in liver fat content (%):

$H_{0CE}: \mu_C - \mu_E,$ $H_{0DE}: \mu_D - \mu_E,$ $H_{0CD}: \mu_C - \mu_D.$

Using the FAS, the secondary hypotheses based on the change from baseline in liver fat content (%) will be analysed using the same method and procedure as in the analysis of the primary variable.

To meet the secondary objectives, we proceed as follows:

If at least one of the three primary hypotheses is rejected, all pairwise comparisons between C, E and D will be carried out with the Tukey method adjusted for 3 multiple comparisons with a Family Wise Error Rate (FWER) of 5%.

|  | Visit | | | | | |
|---|---|---|---|---|---|---|
|  | 1 | 2 | 3 | 4 | 5 | 6 |
|  | Visit window | | | | | |
|  | Screen[a] | Randomisation | Safety follow-up[b] | | End of treatment | Safety follow-up[b] |
|  | | | Week | | | |
|  | −1-(−2) | 0 | 2 | 6 | 12 | 13 |
|  | | | Day | | | |
|  | −3 to −14 | 1 | 15-19 | 40-44 | 80-88 | 87-94 |
| Written informed consent | X | | | | | |
| Inclusion/exclusion criteria | X | X | | | | |
| Demographic data | X | | | | | |
| Medical history | X | | | | | |
| Physical examination | X | | | | | |
| Vital signs | X | | | | X | |
| Weight and other efficacy assessments[c] | X | | | | X | |
| ECG | X | | | | | |
| Concomitant medication | X | X | | X | X | |
| Adverse event | k | X | X | X | X | X[h] |
| Check of SMBG profile[d] | | | X | | | |
| MRI[e] | X | | | | X | |
| OGTT inc glucose, insulin and NEFA[f] | | X | | | X | |
| Samples collection A, see table 3 | X | X | | X[i] | X | |
| Samples collection B, see table 3 | X[j] | | | | X[j] | |
| Samples collection C, see table 3 | X | | | | X | |
| Samples collection D, see table 3 | X | | | | | |
| Samples collection E, see table 3 | X[j] | | | X[j] | X[j] | |
| Samples collection F, see table 3 | X | | | | | |
| Study drug administration | | X | | X | | |

[a] The screen visit (visit 1) may take place during 2 days, especially considering the MRI examination at a separate day. If liver lipids are >5.5% and if inclusion and exclusion criteria are fulfilled the patient will be randomized.

[b] Telephone meeting for safety follow-up. Can be made by study nurse. Visit 6 preferably made 1 week after visit 5.

[c] Weight, height (height only at screening), waist- and hip circumference. Total body fat mass by bioimpedance.

[d] SMBG—Self Monitoring of Blood Glucose. Includes also assessment of U-ketones. Visit will be made as telephone contact by nurse.

[e] MRI assessments - see section 5.1.1. MRI at visit 5 needs to be done before end of treatment, i.e. at least the day before visit 5. Acceptable window for this MRI is up to 6 days before Visit 5.

[f] Plasma samples from inserted catheter into the anticubital vein shall be taken −15, 0, 30, 60 and 120 min after the oral glucose load of 75 g

[g] The End of treatment visit (visit 5) may take place during 2 days, especially considering the MRI examination the day before fasting samples are taken. Last dose of IP will be the day before fasting samples including OGTT.

[h] Extra safety samples will be taken after the study ended if laboratory safety signals have been observed and not resolved during the study, also an additional later time-point may be chosen. Timing of eventual blood sampling after the study will be determined by the study physician. Additional assessments other than laboratory samples may also be made if needed by safety reasons (investigator discretion).

[i] Only P-Glucose, S-Insulin, S-C-peptide, B-HbA1c

[j] Both blood- and urine samples will be obtained. See Table 3 below

[k] SAEs will be recorded from time of informed consent. AEs will be recorded from visit 2 (randomization).

TABLE 3

Laboratory Assessments (collections A-F)

| Collection of analyses Serum/Plasma analytes | Urine analytes |
|---|---|
| Collection A - fasting lipids and glucose | |
| S-triglycerides (fasting), S-total cholesterol, S-HDL-cholesterol (fasting), S-LDL-cholesterol (fasting), S-apoCIII<br>P-Glucose* (fasting), S-Insulin*, S-C-peptide, B-HbA1c<br>S-NEFA* (Non-essential fatty acid) (fasting)<br>*plasma levels of insulin, glucose, and NEFA are also analysed in connection with OGTT | |
| Collection B - fatty acid metabolism and oxidative stress | |
| Free and esterified (=total) P-DHA (docosahexaenoic acid)<br>Free and esterified (=total) P-EPA (eicosapentaneoic acid)<br>Fatty acid composition of cholesteryl esters and phospholipids in plasma | F2 isoprostane and creatinine |
| Collection C - Adipokines and biomarkers of inflammation, oxidative stress, cell death | |
| S-hsCRP, P-Osteopontin, P-Cytokeratin (CK)-18 fragments, including M30, M65, P-FGF-21, P-HMW adiponectin, S-TNF-alpha; S-Leptin, IL-6 | |
| Collection D - metabolomics, proteomics, iron parameters and vit D | |
| Metabolomics, including >500 metabolites<br>Proteomics, including a 92 protein inflammatory chip<br>S-Vitamin D (25-OH)<br>P-Fe, P-Transferrin, P-Ferritin | |
| Collection E - safety parameters and parameters for NAFLD fibrosis score | |
| B-Blood status (incl Hb, RBC, leucocyte count, leucocyte differential count, thrombocyte count) | Dip-stick<br>At visit 1: glucose, ketones, leucocytes, Hb/erythrocytes, protein/albumin<br>At visits made after randomization: only ketones |
| P-Na, P-K, P-Ca, P-Creatinine, P-Cystatin C, P-Glucose | Pregnancy test (only at visit 1 for women of child-bearing potential) |
| S-T4, S-TSH, P-Creatine kinase (CK)<br>P-AST, P-ALT, P-γGT, P-Bilirubin, P-Alkaline phosphatase, P-Albumin | |
| Collection F - genetic testing | |
| Genetic analyses of patients' blood will be performed with a focus on genes related to lipid metabolism, especially liver fat. | |

Example 1b

Further amendments to the study protocol are as follows:

The primary and secondary continuous outcome variables of % liver fat, in the full analysis set, will be analysed on the natural log-scale using a linear mixed effects model. The model will be fitted to the change from baseline in % liver fat at week 12 in the natural log scale with treatment, the natural log of baseline % liver fat (≤/>8%) and eligibility status (pre- or post protocol amendment number 2) as fixed effects, and centres/sites as random effect terms.

The primary hypothesis will be tested using Dunnett's multiple testing procedure with a family-wise error rate of 5%, adjusted for 3 multiple comparisons. Conditional upon rejection of at least one of the three hypotheses for the primary analysis, the secondary hypotheses will be tested using Tukey's multiple testing procedure with a family-wise error rate of 5%, adjusted for three comparisons.

Sample sizes are reduced to n=20 for each group.

The following hypotheses will be tested for the primary hypotheses:

$$H_{0CP}: \mu_C - \mu_P = 0$$

$$H_{0EP}: \mu_E - \mu_P = 0$$

$$H_{0DP}: \mu_D - \mu_P = 0$$

The following hypotheses will be tested for the secondary hypotheses:

$$H_{0CE}: \mu_C - \mu_E = 0$$

$$H_{0DE}: \mu_D - \mu_E = 0$$

$$H_{0CD}: \mu_C - \mu_D = 0$$

Example 2: Pre-Clinical Study

Objective of the Study:

To study the effect of five different SGLT2 inhibitors in combination with Omega-3 free fatty acid Epanova in VCU mice with Non Alcoholic Steato-Hepatitis on the reversal of NASH.

Primary Objective:

To determine the efficacy of Epanova in combination with four different SGLT2 inhibitors on the reduction in NAFLD Activity Score (NAS) in a NASH mouse model.

Model: VCU NASH mouse model.

Diet: High fat and cholesterol diet combined with fructose and glucose

Treatment:

Drugs will administered by daily gavage.

Gavage volume will not exceed 3 mL/kg (60-70 μL/mouse of approximate body weight 20-25 g).

Design:

| | | Week | | | | |
|---|---|---|---|---|---|---|
| | N | −16 | 0 | 8 | 12 | 16 |
| Placebo | n = 10 | | | | | |
| Epanova 400 mg/kg/d | n = 10 | | | | | |
| Dapagliflozin 1 mg/kg/d | n = 10 | | | | | |
| Epanova 400 mg/kg/d + Dapagliflozin 1 mg/kg/d | n = 10 | | | | | |
| Epanova 400 mg/kg/d + Empagliflozin 10 mg/kg/d | n = 10 | | | | | |
| Epanova 400 mg/kg/d + Canagliflozin 1 mg/kg/d | n = 10 | | | | | |
| Epanova 400 mg/kg/d + Ipragliflozin 3 mg/kg/d | n = 10 | | | | | |
| Epanova 400 mg/kg/d + Remogliflozin etabonate | n = 10 | | | | | |

-continued

|  | N | Week | | | |
|---|---|---|---|---|---|
|  |  | −16 | 0 | 8 | 12 | 16 |
| Matching |  | X |  |  |  |  |
| Weight gain |  |  | X | X | X | X |
| Food intake to be weekly |  |  | X | X | X | X |
| Plasma Parameters |  |  | X | X | X | X |
| Liver Histology |  |  |  |  |  | X |
| Sacrifice |  |  |  |  |  | X |

Tail vein or saphena blood samples will be maximally 100 µl per mouse at each occasion. Read out parameters:
1) Body weight at 0, 8, 12 and 16 weeks
2) Food intake at 0, 8, 12 and 16 weeks (per cage; n=3 per group)
3) Plasma total cholesterol and triglycerides at 0, 12 and 16 weeks
4) Lipoprotein profiles at 0, and 16 weeks (cholesterol, triglycerides and phospholipids if possible)
5) Plasma free cholesterol/esterified cholesterol as an indirect measurement of LCAT activity at 0 and 16 weeks
6) ALT and AST levels at 0 and 8, 12, 16 weeks.
7) Plasma PK: levels of DHA and EPA at day 1 and week 16
8) Plasma CK18 at 4, 8. 12 and week 16
9) Liver biopsy w histology week 16
10) Plasma parameters: HbA1c, fructosamine, P-Glucose, ALT, AST
11) Liver weight and lipid content (FC, CE and TG, phospholipids, and FFA profile for EPA and DHA) at sacrifice
12) Faeces collection at 3 weeks (2*48 hr, per cage, n=6 per group) for bomb calorimetric analyses to be performed at AZ.

The pre-clinical study as described above was not carried out. Instead, the pre-clinical studies described in Examples 3 and 4 were carried out.

Example 3: Pre-Clinical Study 2

Effect of SGLT-2 Inhibitors and Epanova Alone or in Combination on Metabolic Parameters and Hepatic Pathology Score in a Mouse DIO-NASH Model Primary Objectives:
Determine the effect of 6 weeks treatment with the SGLT2 inhibitors dapagliflozin, ipragliflozin and canagliflozin and the Omega-3 compound Epanova alone or in combination on NAFLD Activity Score (NAS) including fibrosis stage (post versus pre-treatment) in a diet-induced obese mouse model of fatty liver disease and NASH (DIO-NASH).

Secondary Objectives:
a. Determine the effect of 6 weeks treatment with the SGLT2 inhibitors dapagliflozin, ipragliflozin and canagliflozin and the Omega-3 compound Epanova alone or in combination on terminal hepatic steatosis, inflammation and fibrosis evaluated by (histo)chemical analysis.
b. Determine the effect of 6 weeks treatment with the SGLT2 inhibitors dapagliflozin, ipragliflozin and canagliflozin and the Omega-3 compound Epanova alone or in combination on terminal hepatic triglyceride and cholesterol content evaluated by biochemical analysis.
c. Determine the effect of 6 weeks treatment with the SGLT2 inhibitors dapagliflozin, ipragliflozin and canagliflozin and the Omega-3 compound Epanova alone or in combination on food and water intake, body weight (BW) and body composition.
d. Determine the effect of 6 weeks treatment with the SGLT2 inhibitors dapagliflozin, ipragliflozin and canagliflozin and the Omega-3 compound Epanova alone or in combination on glucose homeostasis (fasting blood glucose (BG)).
e. Determine the effect of 6 weeks treatment with the SGLT2 inhibitors dapagliflozin, ipragliflozin and canagliflozin and the Omega-3 compound Epanova alone or in combination on plasma levels of insulin.
f. Determine the effect of 6 weeks treatment with the SGLT2 inhibitors dapagliflozin, ipragliflozin and canagliflozin and the Omega-3 compound Epanova alone or in combination on plasma levels of alanine aminotransferase (ALT), aspartate aminotransferase (AST), total cholesterol (TC) and triglycerides (TG).
g. Collect terminal plasma for PK analysis.
h. Collect terminal plasma for biomarker analysis.
i. Collect terminal liver for total weight and processing for histology, (bio)chemical and gene expression analysis (optional), and lipid class measurements.
j. Collect adipose tissue depots (epididymal and visceral/mesenteric) for weight and optional gene expression analysis.

Study Outline

| Week −28 | Start DIO-NASH induction |
|---|---|
| Week −3 | NAFLD/NASH screening, pre-biopsy and histology |
| Day −6 | Stratification and randomization |
| Day −5 | EchoMRI scan |
| Day 0 | First dose |
| Day 36 | Echo MRI scan |
| Day 38 | 4 h BG, plasma insulin, TC, TG |
| Day 42 | Termination. Terminal plasma and necropsy |

Materials and Methods
Animals

At 5 weeks of age, C57Bl/6J male mice are purchased from JanVier, France. During the acclimatization and diet-induction period, the mice are group housed five per cage under a 12:12 light dark cycle (lights on from 0400-1600 h) at controlled temperature conditions (22±1° C.; 50±10% relative humidity). Throughout the study period, the mice have ad libitum access to NASH diet (DIO-NASH) (D09100301, Research Diet) (40% fat (18% trans-fat)), 40% carbohydrates (20% fructose) and 2% cholesterol). The animals are kept on the diet for 28 weeks before experimentation. In addition, a sub-set of animals are given normal chow (Altromin 1324, Brogaarden) to be included as a lean control group (LEAN-CHOW). During post-OP recovery and study period, animals will be single-housed. BW will be recorded once daily during the study period. 24 h food and water intake will be recorded once weekly during the study period.

DIO-NASH Induction, Stratification, Randomization and Baseline Monitoring

During the DIO-NASH diet-induction period, BW will be monitored once monthly. After 25 weeks of diet-induction, a liver biopsy will be obtained for hepatic progression of fibrosis and steatosis evaluated by histochemical analysis, and subsequently NAFLD Activity Score including fibrosis stage and optional gene expression analysis (see below). At day −6, animals are stratified into treatment groups according to levels of fibrosis (% collagen) followed by randomization based on 1) liver fibrosis and 2) BW. In addition, liver steatosis (% lipid) will be analyzed. At day −5, animals are EchoMRI scanned for body composition analysis.

Study Groups

Animals are randomized into 8+1 study groups (n=10):

| Group 1 | DIO-NASH - Vehicle (QD, PO) |
| Group 2 | DIO-NASH - Dapagliflozin, 1 mg/kg (QD, PO) |
| Group 3 | DIO-NASH - Epanova, 600 mg/kg (QD, PO) |
| Group 4 | DIO-NASH - Dapagliflozin (1 mg/kg) + Epanova (600 mg/kg) (QD, PO) |
| Group 5 | DIO-NASH - Ipragliflozin, 3 mg/kg (QD, PO) |
| Group 6 | DIO-NASH - Ipragliflozin (3 mg/kg) + Epanova (600 mg/kg) (QD, PO) |
| Group 7 | DIO-NASH - Canagliflozin, 30 mg/kg (QD, PO) |
| Group 8 | DIO-NASH - Canagliflozin (30 mg/kg) + Epanova (600 mg/kg) (QD, PO) |
| Group 9 | LEAN-CHOW - Control |

Dosing volume is 5-20 ml/kg (TBD). Route of administration is per oral (PO) dosing by gavage. Dosing frequency will be once daily (QD). Day 0 is the first day of dosing. Animals are dosed with compound(s) and vehicle between 2-4 PM. Animals are dosed for 42 days. Last dose will be administered the day before termination (study day 41).

Body Weight, Food and Water Intake

Body weight will be recorded once daily during the study period upon dosing. Food and water intake are measured once weekly (24 h intake) during the study period.

Compound Preparation

SGLT2-inhibitors dapagliflozin, ipragliflozin and canagliflozin are dissolved in PBS with final concentrations of 0.2 mg/ml, 0.6 mg/ml and 6 mg/ml, respectively, for a dosing volume of 5 ml/kg (alternatively 10 or 20 ml/kg (TBD)). Omega-3 compound Epanova will be provided in capsules (1 g; approx 800 mg Omega-3). Vehicle will be olive oil and PBS. Epanova compound will be prepared by aspirating the content of 2 capsules (approx 1600 mg Omega-3) for dissolving in 13 ml olive oil to obtain a final concentration of approx 120 mg/ml for a dosing volume of 5 ml/kg (alternatively 10 or 20 ml/kg (TBD)).

Hepatic Pre-Screening for Assessment of Steatosis and Fibrosis Levels

Biopsy preparation for hepatic pre-screening: After overnight storage in 4% PFA, liver biopsies are infiltrated over-night in paraffin in an automated Miles Scientific Tissue-TEK VIP Tissue Processor and subsequently embedded in paraffin blocks. These are then trimmed and one 5 μm section per biopsy is cut (for Sirius Red staining) on a Microm HM340E Microtome (Thermo Scientific). Additionally extra sections for each biopsy are taken in order to compare pre-biopsy with the whole liver at the end of the study regarding histological assessment (NAFLD Activity Score including fibrosis stage) (see below). 5 sections (one per biopsy) are embedded on one block and two blocks are placed on one slide giving a total of 10 biopsy sections per slide. Sections are left to dry overnight. To assess hepatic steatosis and fibrosis sections are stained with Sirius Red and analyzed by Visiomorph software (Visiopharm, Copenhagen, Denmark). Pre-biopsy assessment of hepatic steatosis and fibrosis will be described as % of total area.

Final Blood Glucose and Plasma Sampling

Blood samples for measuring 4 h fasting BG will be collected at study day 38. In addition, plasma will be obtained at study day 38 for determination of 4 h fasting plasma insulin, TC and TG. Animals will be fasting from 6 AM-10 AM and blood samples will subsequently be collected from the tail vein (by snipping) for blood glucose and plasma insulin determination and from the submandibular (cheek) vein for plasma TC and TG analysis.

Body Composition

Body composition will be analyzed prior to study start at day −5 and at study day 36 by non-invasive EchoMRI-900 (EchoMRI, USA). The scanner measure fat and lean tissue mass. During the scanning procedure, the mouse is placed in a restrainer for 90-120 seconds.

Termination

Animals will be terminated at study day 42 in a non-fasting state.

Lipid Class Analysis of Liver Samples

Liver tissue (approx 50 mg) are excised at necropsy and rapidly weighed and immediately transferred to a 2-ml homogenization tube and snap-frozen in liquid nitrogen.

Liver Tissue Processing

Pre-Study Biopsy:

Approximately three weeks before study start, a wedge of liver tissue (~100 mg) is excised from the distal portion of the left lateral lobe, divided in two pieces and immediately placed in either 4% paraformaldehyde (2/3) or in RNAlater (1/3).

Terminal Liver Tissue:

Following 6 weeks of treatment, the whole liver is collected, weighed and liver biopsies from the left lateral lobe are excised and immediately placed in 4% paraformaldehyde (~100 mg), RNAlater (~50 mg) and a piece (~100 mg) collected in FastPrep tube and snap-frozen in liquid nitrogen.

Fixation, Embedment and Sections:

Following an over-night fixation in 4% phosphate buffered formaldehyde (10% formalin), liver biopsies are infiltrated over-night in paraffin in an automated Miles Scientific Tissue-TEK VIP Tissue Processor and subsequently embedded in paraffin blocks. Five biopsied are embedded in one block. The blocks are trimmed and four 5 μm section per block is cut on a Microm HM340E Microtome (Thermo Scientific). One section from two different blocks is placed on one object slide giving a total of 10 biopsy sections per slide.

Tissue Homogenation:

1 mL 5% NH-40/ddH$_2$O solution (ab142227, Abcam) is added to the fast FastPrep tube. The tubes are placed in a FastPrep homogenizer and shaked for 2×60 seconds. After homogenization the samples are slowly heated to 80-100° C. in a heating block for 3 minutes. After being cooled to room temperature the heating step is repeated. The samples are centrifuged for two minutes at top speed using a microcentrifuge to remove any insoluble material. The supernatant is stored at −80° C. until usage.

NAFLD Activity Score (NAS) and Fibrosis Stage

A liver pre-biopsy and terminal liver tissue from the left lateral lobe will be collected for NAS and assessment of fibrosis stage by use of clinical criteria outlined by Kleiner and colleagues (Design and validation of a histological scoring system for nonalcoholic fatty liver disease, Kleiner et al, Hepatology 41; 2005). The NAS is the sum of steatosis, lobular inflammation and hepatocellular ballooning scores:

Histology: Steatosis, Ballooning Degenerating, Inflammation and Fibrosis

Biopsy Preparation for Hepatic Histopathological Screening:

To assess hepatic steatosis, ballooning degeneration, fibrosis and inflammation sections are stained with H&E, Sirius Red, CK18 (ballooning) and Galectin-3 (macrophages), respectively) followed by analysis with Visiomorph software (Visiopharm, Copenhagen, Denmark). Biopsy assessment of hepatic steatosis, fibrosis or inflammation will be described as percentage of total area using a protocol designed for the specific purpose.

HE Staining:

In brief, paraffin embedded sections are de-paraffinated in xylene and rehydrated in series of graded ethanol. Sections are then incubated for 5 min in Mayer's Hematoxylin (Cat no. MHS80 2.5 L, Sigma Aldrich), washed for 5 min in running tap water and then stained for 5 min in Eosin Y solution (Cat. No. HT110280 2.5 L, Sigma-Aldrich). Slides are hydrated, mounted with Pertex and allowed to dry before scanning Sirius red: In brief, paraffin embedded sections are de-paraffinated in xylene and rehydrated in series of graded ethanol. The slides are stained in picro-sirius red for one hour and washed two times in acidified water. The remaining water is removed by vigorously shaking the slides. Thereafter the slides are hydrated in three changes of 100% ethanol, cleared in xylene and mounted with Pertex and allowed to dry before scanning CK18 and Galectin-3 immunohistochemistry: A commercial CK18 and Galectin-3 antibody will be applied using standard procedures. In short, paraffin embedded sections are de-paraffinated in xylene and rehydrated in series of graded ethanol before antigen retrieval in boiling tris-EGTA buffer (pH 9) or by proteinase K treatment. Sections are rinsed in wash buffer (TBS+Tween 20, TBS-T) between all steps. Endogenous peroxidase activity is quenched in 1% H2O2 followed by serum blocking in a solution containing 5% normal swine serum, 1% bovine serum albumin, and 0.2% Tween 20. Sections are then incubated for 1 hr with the primary antibody diluted in serum blocking solution and subsequently incubated with the secondary antibody. The antibody signal is amplified using the Envision+HRP-coupled polymer system (Dako) and visualized in a DAB solution, producing a distinct brown staining of macrophages.

All slides are finally digitized under a 20× objective in an Aperio Scanscope AT slide scanner for image analysis.

Chemistry: Hepatic Hydroxyproline Content 50 mg formalin fixed liver tissue is homogenized in 500 μl water. 500 μl concentrated hydrochloric acid is added and the samples hydrolyzed at 120 C for 3 hours. The supernatant is transferred to a 96 well plate and wells are evaporated to dryness over night. Total collagen content in the liver is measured by colorimetric determination of hydroxyproline residues by acid hydrolyxix of collagen (Cat no. MAK008, Sigma Aldrich).

Biochemistry: Hepatic Triglycerides and Cholesterol Content

Triglycerides and cholesterol content in liver homogenates is measured in single determinations using autoanalyzer Cobas C-111 with commercial kit (Roche Diagnostics, Germany) according to manufacturer's instructions.

Data, Reporting, and Statistical Evaluation

Results are presented as mean±SEM (standard error of the mean) unless otherwise stated. Statistical evaluation of the data is carried out using Student's unpaired t-test or two-way ANOVA for comparison of LEAN-CHOW control versus DIO-NASH Vehicle. For comparison of DIO-NASH groups, one-way and two-way ANOVA are being applied where appropriate. Post-hoc analysis (Dunnett/Bonferroni) in cases with statistical significance is performed (p<0.05 considered significant).

Results

The study results are shown in FIGS. 1 and 2:

FIG. 1 shows the effects of Dapagliflozin (B), Epanova (C), Ipragliflozin (E), Canagliflozin (G) alone and combinations of Epanova with Dapagliflozin (D), Ipragliflozin (F) and Canagliflozin (H) compared with a the control group given vehicle (A) on NAFLD activity score. Statistical analysis was done by Kruskal-Wallis non-parametric ANOVA, followed by a post-hoc test comparing the control group with the other groups. A p-value<0.05 was regarded as significant. The p-value of Kruskal-Wallis test was <0.01, while the post hoc test was not significant.

FIG. 2 shows effects of Dapagliflozin (B), Epanova (C), Ipragliflozin (E), Canagliflozin (G) alone and combinations of Epanova with Dapagliflozin (D), Ipragliflozin (F) and Canagliflozin (H) compared with a the control group given vehicle (A) on fibrosis stage. Statistical analysis was done by Kruskal-Wallis non-parametric ANOVA, followed by a post-hoc test comparing the control group with the other groups. A p-value<0.05 was regarded as significant. The p-value of Kruskal-Wallis test was non-significant (p=0.4).

Summary of Results:

No effects on the primary effect variables; NAFLD activity scores or fibrosis stage of either Epanova, dapagliflozin or the combination at the end of the study Comparing baseline and end-of study biopsies Epanova and the combination reduced NAFLD activity score Comparing baseline and end-of study biopsies, dapagliflozin reduced fibrosis Example 4: Pre-Clinical Study 3

A further pre-clinical mouse study was carried out according to the Experimental plan described below:

Experimental Plan

Model: VCU (Virginia Commonwealth University) NASH mouse model; inbred C57bI6J/×129SI/SvlmJ given high fat, cholesterol, fructose and glucose diet for 16 weeks before starting pharmacological treatment.

Treatment: drugs will be administered by daily gavage. Gavage volume will not exceed 3 mL/Kg. vehicles will be olive oil and water. Epanova and dapagliflozin will be administered by daily gavage in one syringe.

Design:

Run-in: 16 weeks in high fat, cholesterol, fructose and glucose diet one week with vehicle gavage.

T=0 weeks: the mice will be matched based on body weight. The mice will be divided into 4 groups of 12 animals. Vehicle gavage for one week before commencing active treatment for 4 weeks.

Groups

| Control: | olive oil and water | n = 12 |
| Epanova: | 600 mg/Kg/d and water | n = 12 |
| Dapagliflozin: | 1 mg/kg/d and olive oil | n = 12 |
| Epanova + dapa: | 600 mg/kg/d and 1 mg/kg/d | n = 12 |

| Procedures | week | | | | | |
|---|---|---|---|---|---|---|
| | −16 | 0 | 1 | 2 | 3 | 4 |
| Start diet | X | | | | | |
| Matching | | X | | | | |
| Vehicle gavage | | X | | | | |
| Treatment | | | X | X | X | X |
| Weight (q week) | X | X | X | X | X | X |
| Plasma samples | | | | | | X |
| Sacrifice | | | | | | X |

Plasma Analyses:
a) Hepatic panel (ALT and AST, ALP)
b) Lipid panel (total cholesterol and triglycerides)
c) Plasma PK: levels of total plasma fatty acid composition and dapagliflozin
d) glucose and insulin
e) inflammatory parameters and oxidative stress biomarkers Results The study results are shown in FIGS. 3 and 4:

FIG. 3: Effects of Epanova (Epa), Dapagliflozin (Dapa) and the combination of Epanova and Dapagliflozin (Epa+Dapa) on histological assessment of steatosis (A), inflammation (B), ballooning (C) and the sum of these assessments given as NAFLD activity score (D). A p-value<0.05 was regarded as significant. * p<0.05 vs Control FIG. 4: Effects of Epanova (Epa), Dapagliflozin (Dapa) and the combination of Epanova and Dapagliflozin (Epa+Dapa) on histological assessment of stage of fibrosis.

A p-value<0.05 was regarded as significant. * p<0.05 vs Control

Summary of Results:
Epanova reduced NAFLD Activity Score with significant effect on steatosis, and a trend towards an effect on ballooning
Epanova reduced fibrosis stage
Dapagliflozin alone had no effect
Dapagliflozin had no effects on top of Epanova alone
Some aspects of the disclosure include:

1. A combination of an SGLT-2 inhibitor with an omega-3 fatty acid composition (wherein the omega-3 fatty acid composition comprises one or more omega-3 fatty acids which may be present as acids, esters, triglycerides, phospholipids or salts).
2. A combination as described in aspect 1, wherein the omega-3 fatty acid composition is provided as an OM3-CA product, such as Epanova® or a bio-equivalent version thereof.
3. A combination as described in aspect 2 wherein the SGLT-2 inhibitor is selected from dapagliflozin, canagliflozin, remogliflozin etabonate, ipragliflozin and empagliflozin.
4. A combination as described in aspect 3 wherein the SGLT-2 inhibitor is dapagliflozin.
5. A combination as described in aspect 1 wherein the omega-3 fatty acid composition is provided as an OM3-EE product, such as Lovaza® or Omtryg® or a bioequivalent version of any of these.
6. A combination as described in aspect 1 wherein the omega-3 fatty acid composition is provided as an icosapent ethyl product, such as Vascepa® or a bio-equivalent version thereof.
7. A combination as described in aspect 6 wherein the SGLT-2 inhibitor is selected from dapagliflozin, canagliflozin, remogliflozin etabonate, ipragliflozin and empagliflozin.
8. A combination as described in aspect 7 wherein the SGLT-2 inhibitor is dapagliflozin.
9. A method for treating NAFLD and/or NASH comprising administering an effective dose of a combination as described in any one of aspects 1 to 8 to a warm-blooded animal in need of such treatment.
10. A combination as described in any one of aspects 1 to 8 for use as a medicament.
11. A combination as described in any one of aspects 1 to 8 for use as a medicament for the treatment of NAFLD and/or NASH.
12. A combination as described in aspect 11 for the treatment of NAFLD and/or NASH in a human diagnosed as suffering from type II diabetes.
13. A combination as described in aspect 11 or 12 for the treatment of NAFLD and/or NASH in a human diagnosed as having pancreatic exocrine insufficiency.

What is claimed is:

1. A combination of an effective dose of an omega-3 fatty acid composition, and an effective dose of dapagliflozin or a pharmaceutically acceptable salt thereof, for the treatment of non-alcoholic steatohepatitis (NASH) in a subject having, or suspected of having, NASH;
   wherein the omega-3 fatty acid composition comprises:
   about 50-60 wt % eicosapentaenoic acid (EPA);
   about 15-25 wt % docosahexaenoic acid (DHA);
   about 1 to 8 wt % docosapentaenoic acid (DPA);
   wherein at least 90 wt % of the polyunsaturated fatty acid in the composition is present in free acid form.

2. A method of treating NASH comprising:
   selecting a subject having, or suspected of having NASH on the basis of their non-alcoholic fatty liver disease (NAFLDU) Activity Score;
   administering the combination of claim 1; and
   thereby improving the NAFLD Activity Score of said subject by at least 1 point, with no worsening of the subject's fibrosis stage score.

3. The method of claim 2, wherein the subject's NAFLD Activity Score is greater than or equal to 5.

4. The combination of claim 1 wherein the subject has been diagnosed with Type II diabetes mellitus.

5. A combination of an effective dose of an omega-3 fatty acid composition and an effective dose of dapagliflozin or a pharmaceutically acceptable salt thereof, for the reduction of liver fat in a subject who has been diagnosed with Type II diabetes mellitus and diagnosed as having raised liver fat;
   wherein the omega-3 fatty acid composition comprises:
   about 50-60 wt % EPA;
   about 15-25 wt % DHA;
   about 1 to 8 wt % DPA;
   wherein at least 90 wt % of the polyunsaturated fatty acid in the composition is present in free acid form.

6. The combination of claim 5, wherein the combination also causes a reduction in plasma triglyceride level in the subject.

7. The combination of claim 5, wherein the combination also causes a raising of plasma EPA and/or DHA levels in the subject.

8. The combination of claim 5, wherein the combination also causes a reduction of cell death and/or ballooning in the subject.

9. The combination of claim 5, wherein the subject has a Body Mass Index (BMI)>25.

10. A combination comprising an omega-3 fatty acid composition and dapagliflozin or a pharmaceutically acceptable salt thereof;

wherein the omega-3 fatty acid composition comprises:
about 50-60 wt % EPA;
about 15-25 wt % DHA;
about 1 to 8 wt % DPA:
wherein at least 90 wt % of the polyunsaturated fatty acid in the composition is present in free acid form.

11. The combination of claim 10, wherein the omega-3 fatty acid composition is present in an amount of 1 g, 2 g or 4 g.

12. The combination of claim 10, wherein dapagliflozin or a pharmaceutically salt thereof is present in an amount of 5 or 10 mg.

13. A method for the reduction of liver fat and the reduction of liver inflammation in a subject in need thereof, comprising administering the combination of claim 10 to the subject.

14. A method for halting progression of liver fibrosis in a subject in need thereof, comprising administering the combination of claim 10 to the subject.

15. A method for halting progression of NAFLD and/or NASH thereby causing a halt in progression of fibrosis of the subject's liver in a subject who has been diagnosed with NAFLD or NASH, comprising administering the combination of claim 10 to the subject.

16. A method for the treatment of NASH, in a subject having, or suspected of having NASH, comprising administering the combination of claim 10, and thereby causing a reduction in body weight of the subject.

17. A method for wherein the treatment of NASH, in a subject having, or suspected of having NASH, comprising administering the combination of claim 10, and thereby causing an increase in insulin sensitisation of the subject.

* * * * *